United States Patent [19]
Kawaguchi et al.

[11] Patent Number: 6,114,529
[45] Date of Patent: Sep. 5, 2000

[54] S TYPE 2-SUBSTITUTED HYDROXY-2-INDOLIDINYLBUTYRIC ESTER COMPOUNDS AND PROCESS FOR PREPARATION THEREOF

[75] Inventors: Takayuki Kawaguchi, Tokyo-to; Sumihiro Nomura, Kawaguchi; Kenji Tsujihara, Urawa, all of Japan

[73] Assignee: Tanabe Seiyaku Co., Ltd., Osaka, Japan

[21] Appl. No.: 09/421,335

[22] Filed: Oct. 18, 1999

Related U.S. Application Data

[62] Division of application No. 09/172,666, Oct. 15, 1998, Pat. No. 6,015,901.

[30] Foreign Application Priority Data

Oct. 30, 1996 [JP] Japan .................................. 8-288074

[51] Int. Cl.[7] ....................... C07D 471/20; C07D 471/22
[52] U.S. Cl. ................................. 546/15; 546/18
[58] Field of Search ........................ 546/15, 18

[56] References Cited

U.S. PATENT DOCUMENTS 5,053,512  10/1991  Wani et al. ............................... 546/41

FOREIGN PATENT DOCUMENTS

| 0220601 | 5/1987 | European Pat. Off. . |
|---|---|---|
| 296597 | 12/1988 | European Pat. Off. . |
| 418099 | 5/1991 | European Pat. Off. . |
| 0471358 | 2/1992 | European Pat. Off. . |
| 540099 | 5/1993 | European Pat. Off. . |
| 0556585 | 8/1993 | European Pat. Off. . |
| 0757049 | 2/1997 | European Pat. Off. . |
| 0781781 | 7/1997 | European Pat. Off. . |
| 5279369 | 10/1993 | Japan . |
| 687746 | 3/1994 | Japan . |
| 9008479 | 10/1990 | South Africa . |
| 9003169 | 4/1990 | WIPO . |
| WO9105556 | 5/1991 | WIPO . |
| 9316698 | 9/1993 | WIPO . |
| WO9631513 | 10/1996 | WIPO . |

OTHER PUBLICATIONS

Bioorganic & Medicinal Chemistry Letter, vol. 5, No. 24, pp. 3063–3066, (1995).
Journal of Medicinal Chemistry, (1986,) vol. 29, pp. 2358–2363.
Journal of Medicinal Chemistry, (1980,) vol. 23, pp. 554–560.
Journal of Medicinal Chemistry, (1991,) vol. 34, pp. 98–107.
Organic Synthetic Chemistry, vol. 49, No. 11, pp. 1013–1020, (1991).
Ejima et al., "Antitumor Agents, Part 2. Asymmetric Synthesis of (S)–Camptothecin" No. 1, pp. 27–31, XP002010690 (1990), J. Chem. Soc. Perkin Trans.
Mash et al., "Mechanistic Studies of Disastereoselective Cyclopropanation via Homochiral Ketals. 2. Studies with Conformationally Restricted 2–Cyclohexene–1–one Ketals", vol. 55, No. 7, pp. 2055–2060, XP002054434 (1990), J. Org. Chem.
Ejima et al., "Asymmetric Synthesis of (S)–Camptothecin" Tetrahedron Lett, vol. 30, No. 20, pp. 2639–2640, XP002054435 (1989).
Ejima et al., "Antitumor Agents v. Synthesis and Antileukemic Activity of E–Ring–Modified (RS)–Campothecin Analogues" Chem. Pharm. Bull., vol. 40, No. 3, pp. 683–688, XP000653713 (1992).
Wall et al., J. Med. Chem., vol. 29, No. 8, (1986), pp. 1553–1555.
Wani et al., J. Med. Chem., vol. 30, No. 12, (1987), pp. 2317–2319.
Patent Abstracts of Japan, vol. 016, No. 528, Oct. 29, 1992 (Publication No. 04200393 dated Jul. 21, 1992).
Patent Abstracts of Japan, vol. 016, No. 528, Oct. 29, 1992 (Publication No. 04200392 dated Jul. 21, 1992).
Ejima et al., Chem. Pharm. Bull., vol. 37, No. 8, (1989), pp. 2253–2255.

(List continued on next page.)

Primary Examiner—Laura L. Stockton
Attorney, Agent, or Firm—Birch, Stewart, Kolasch & Birch, LLP

[57] ABSTRACT

A process for preparing S type 2-substituted hydroxy-2-indolidinyl-butyric ester compound [II]:

wherein $R^0$ is residue of nitrogen-containing fused heterocyclic carboxylic acid having absolute configuration of "R"(in which the nitrogen atom is protected), $R^1$ and $R^2$ are lower alkyl group, and E is ester residue, which is useful as an intermediate for preparing camptothecin derivatives having antitumor activities, which comprises 2-ethylating 2-substituted hydroxy-2-indolidinylacetic ester compound [I]:

wherein the symbols are as defined above.

11 Claims, No Drawings

OTHER PUBLICATIONS

Terasawa et al., Chem. Pharm. Bull., vol. 37, No. 12, (1989), pp. 3382–3385.

Jew et al., Tetrahedron: Asymmetry, vol. 6, No. 6, (1995), pp. 1245–1248.

Kurihara et al., J. Heterocycl. Chem., vol. 30, No. 3, (1993), pp. 643–652.

S TYPE 2-SUBSTITUTED HYDROXY-2-INDOLIDINYLBUTYRIC ESTER COMPOUNDS AND PROCESS FOR PREPARATION THEREOF

This application is a divisional of co-pending Application Ser. No. 09/172,666, filed on Oct. 15, 1998, now U.S. Pat. No. 6,015,901, the entire contents of which are hereby incorporated by reference.

FIELD OF INVENTION

This invention relates to an S type 2-substituted hydroxy-2-indolidinylbutyric ester compound and a process for the preparation thereof. More particularly, it relates to an S type 2-substituted hydroxy-2-indolidinyl-butyric ester compound which is useful as an intermediate for preparing camptothecin derivatives having antitumor activities and a process for preparing said compound in high yield and in high stereoselectivity.

PRIOR ART

There is known a process for preparing camptothecin derivatives having antitumor activities by Friedlaender reaction (cf. EP-A-540099, EP-A-296597, JP-A-6-87746, WO 90/03169, EP-A-418099), wherein it has been investigated to find processes for preparing S type 4-hydroxypyranoindolidine compounds of the formula [VIII] which are important as an intermediate:

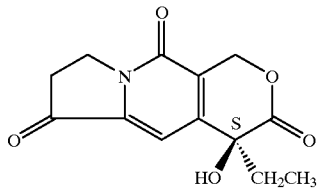

[VIII]

Besides, it is reported, for example, in EP-A-220601 that an S type 2-[(R)-N-tosyl-prolyloxy]-2-indolidinylbutyric ester compound of the formula [XXI]:

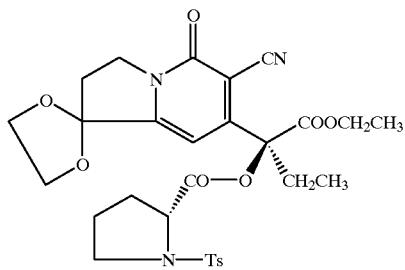

[XXI]

may be prepared by brominating at 2-position of a 2-indolidinylacetic ester compound of the formula [XX]:

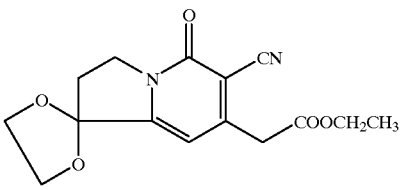

[XX]

and reacting the resultant with an (R)-N-tosylproline and further ethylating at 2-position of the reaction product, and further that a camptothecin derivative is prepared from said compound via an S type 4-hydroxypyranoindolidine compound [VIII].

However, according to this process, the desired S type 2-[(R)-N-tosylprolyloxy]-2-indolidinylbutyric ester compound [XXI] is merely obtained in an amount of 2.6–4.6 times larger (44–64% d.e.) than that of a diastereomer having an absolute configuration of "R" at 2-position which is simultaneously prepared, and the S type compound is isolated therefrom in a further lower yield, only 56%, by a fractional recrystallization [cf. Organic Synthetic Chemistry, vol. 49, No. 11, pp. 1013–1020,1991].

BRIEF SUMMARY OF THE INVENTION

This invention provides an S type 2-substituted hydroxy-2-indolidinylbutyric ester compound useful as an intermediate for preparing camptothecin derivatives in a high yield and in a high stereoselectivity.

DETAILED DESCRIPTION OF THE INVENTION

According to this invention, the desired S type 2-substituted hydroxy-2-indolidinylbutyric ester compound of the formula [II]:

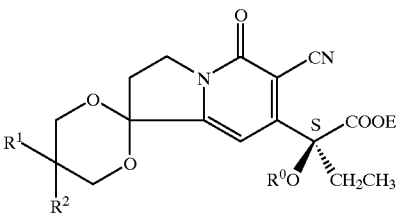

[II]

can be prepared by reacting a 2-halo-2-indolidinylacetic ester compound of the formula [III]:

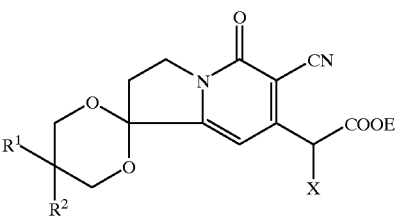

[III]

wherein X is a halogen atom, $R^1$ and $R^2$ are a lower alkyl group, and E is an ester residue, with an R type nitrogen-containing fused heterocyclic carboxylic acid compound of the formula [IV]:

$R^0OH$ [IV]

wherein R⁰ is a residue of a nitrogen-containing fused heterocyclic carboxylic acid having an absolute configuration of "R" which is obtained by removing hydroxy group from the carboxyl group of said carboxylic acid compound (in which the nitrogen atom contained in the residue is protected) or a salt thereof to give a 2-substituted hydroxy-2-indolidinylacetic ester compound of the formula [I]:

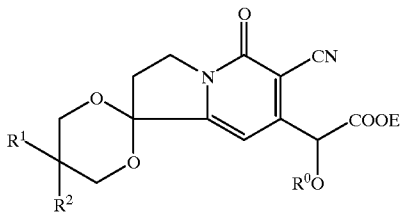

[I]

wherein the symbols are as defined above, and then ethylating 2-position of the resultant compound [I].

The process of this invention is characteristic in that the 2-substituted hydroxy-2-indolidinylacetic ester compound [I] is sterically bulky at the acetal moiety and has a sterically bulky substituent containing an optically active nitrogen-containing fused heterocyclic ring at 2-position thereof and hence it is ethylated with high yield and high stereoselectivity at 2-position, and thereby the desired S type 2-substituted hydroxy-2-indolidinylbutyric ester compound [II] is obtained in a high selectivity such as 9 times or more higher (80% d.e. or more) than the diastereomer having an absolute configuration of "R" at 2-position. Particularly, when the group "Y" in the substituent R⁰ in the compound [I] is a 4-nitrophenylsulfonyl group or a 4-biphenyl sulfonyl group, the desired compound is obtained in much higher stereoselectivity of 20 times (90% d.e.) or 15.2 times (88% d.e.) higher, respectively and in much higher isolation yield of 75% or 76%, respectively.

The R type nitrogen-containing fused heterocyclic carboxylic acid compound [IV] in this invention means a compound having a carboxyl group bound to a nitrogen-containing fused heterocyclic ring (the nitrogen atom contained in said compound is protected), and the carbon atom bound with the carboxyl group has an absolute configuration of "R", and the nitrogen-containing fused heterocyclic ring includes a benzene-fused nitrogen-containing heterocyclic ring, for example, a tetrahydroisoquinoline ring, a tetrahydroquinoline ring, a dihydroquinoline ring, or an indoline ring.

Suitable example of the nitrogen-containing fused heterocyclic carboxylic acid compound having an absolute configuration of "R" is a compound of the formula [XIX]:

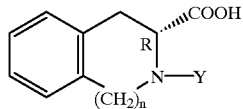

[XIX]

wherein n is 0 or 1, and Y is a substituted or unsubstituted arylsulfonyl group or a lower alkylsulfonyl group.

The above compound [XIX] wherein n is 1 means an N-substituted-1,2,3,4-tetrahydro-3-ylquinolinecarboxylic acid, and the compound [XIX] wherein n is 0 means an N-substituted 2-indolinecarboxylic acid. The substituent "Y" on the nitrogen atom of the above compound [XIX] includes a phenylsulfonyl, naphthylsulfonyl or biphenylyl-sulfonyl group (which may optionally be substituted by a member selected from a nitro group, a lower alkyl group, a lower alkoxy group, a cycloalkyl group, a halogen atom, or a thienyl group), or a lower alkylsulfonyl group, for example, a phenylsulfonyl group, a tosyl group, a 2,4,6-trimethylphenylsulfonyl group, a 4-nitrophenylsulfonyl group, a 4-chlorophenylsulfonyl group, a 4-methoxyphenylsulfonyl group, a 4-cyclohexylphenylsulfonyl group, a 4-(3-thienyl) phenylsulfonyl group, a 2-naphthylsulfonyl group, a 4-biphenylylsulfonyl group, a methylsulfonyl group, and an ethylsulfonyl group.

Among the above, preferred compounds are a compound [XIX] wherein the substituent "Y" on the nitrogen atom is a tosyl group, a 2-naphthyl-sulfonyl group, a 2,4,6-trimethylphenylsulfonyl group, a 4-biphenylylsulfonyl group, or a 4-nitrophenylsulfonyl group and n is 1, and a compound [XIX] wherein the substituent "Y" on the nitrogen atom is a tosyl group and n is 0. Particularly preferred compounds are a compound [XIX] wherein the substituent "Y" on the nitrogen atom is a 4-biphenylylsulfonyl group or a 4-nitrophenylsulfonyl group and n is 1.

The R¹ and R² are a lower alkyl group, such as a methyl group, an ethyl group, a propyl group, an isopropyl group, an n-butyl group, an isobutyl group; X is a halogen atom such as chlorine, bromine, iodine. The E includes any conventional ester residues, for example lower alkyl groups such as a methyl group, an ethyl group, a propyl group, an isopropyl group, an n-butyl group, or an isobutyl group. Among them, preferable groups are R¹ and R² being a methyl group, X being a chlorine atom or a bromine atom, and E being a methyl group or an ethyl group.

The reaction of the 2-halo-2-indolidinylacetic ester compound [III] and the R type nitrogen-containing fused heterocyclic carboxylic acid compound [IV] or a salt thereof is carried out in a suitable solvent.

The salt of the R-type nitrogen-containing fused heterocyclic carboxylic acid compound [IV] includes an alkali metal salt (e.g. potassium salt, sodium salt), an alkaline earth metal salt (e.g. magnesium salt, calcium salt).

The reaction of the 2-halo-2-indolidinylacetic ester compound [III] and the R type nitrogen-containing fused heterocyclic carboxylic acid compound [IV] or a salt thereof is preferably carried out in the presence or absence of an acid scavenger. Suitable examples of the acid scavenger are inorganic bases, such as an alkali metal hydride (e.g. lithium hydride, sodium hydride, potassium hydride), an alkali metal amide (e.g. lithium amide, sodium amide, potassium amide), an alkali metal carbonate (e.g. sodium carbonate, potassium carbonate), an alkali metal hydrogen carbonate (e.g. sodium hydrogen carbonate, potassium hydrogen carbonate), an alkali metal hydroxide (e.g. sodium hydroxide, potassium hydroxide, lithium hydroxide), and organic bases, such as an alkali metal alkoxide (e.g. sodium ethoxide, potassium tert-butoxide), an alkali metal alkylamide (e.g. lithium diisopropylamide), a trialkylamine (e.g. triethylamine, trimethylamine), an N,N-dialkylaniline (e.g. N,N-dimethylaniline), 1,8-diazabicyclo [5.4.0]undeca-7-ene.

The solvent used in the reaction includes any conventional solvent which does not affect on the reaction, and suitable examples are an amide type solvent (e.g. dimethylformamide, dimethylacetamide), an ether solvent (e.g. tetrahydrofuran, dimethyl ether, dioxane). The reaction is usually carried out at a temperature of from 20 to 100° C., preferably from 50 to 70° C.

The subsequent 2-ethylation of the 2-substituted hydroxy-2-indolidinylacetic ester compound [I] is carried out in a suitable solvent in the presence of an acid scavenger.

The ethylating agent is preferably an ethyl halide (e.g. ethyl iodide, ethyl bromide), more preferably ethyl iodide. The acid scavenger is the same agents as mentioned above for the reaction of the 2-halo-2-indolidinylacetic ester compound [III] and the R type nitrogen-containing fused heterocyclic carboxylic acid compound [IV] or a salt thereof, and particularly preferable agent is sodium hydride.

The solvent used in the reaction includes any conventional solvent which does not affect on the reaction, and suitable examples are an amide type solvent (e.g. dimethylformamide, dimethylacetamide), a sulfoxide solvent (e.g. dimethylsulfoxide), an ether solvent (e.g. tetrahydrofuran, dioxane, dimethyl ether), an aromatic hydrocarbon solvent (e.g. toluene, xylene, benzene, chlorobenzene), or a mixture thereof, and particularly preferable solvent is a mixture of dimethylacetamide and toluene. The reaction is usually carried out at a temperature of from −10 to 50° C., particularly preferably at a room temperature.

The desired compound [II] in a crude form thus obtained can easily be purified by recrystallization to give a highly purified compound [II].

The S type 2-substituted hydroxy-2-indolidinylbutyric ester compound [II] thus obtained is subjected to a catalytic reduction to reduce the cyano group thereof and then subjected to alkanoylation to give an S type 2-substituted hydroxy-2-(6-substituted aminomethylindolidinyl)butyric ester compound of the formula [V]:

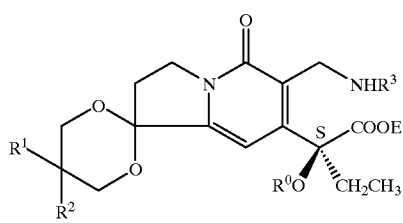

[V]

wherein $R^3$ is a lower alkanoyl group, and other symbols are as defined above, and the resultant is subjected to nitrosation reaction and rearrangement to give an S type 2-substituted hydroxy-2-(6-substituted hydroxymethylindolidinyl)-butyric ester compound of the formula [VI]:

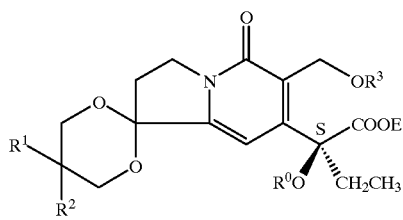

[VI]

wherein the symbols are as defined above. The compound [VI] is then subjected to an intramolecular cyclization reaction, and thereafter or at the same time as the cyclization reaction, the acetal group thereof is converted into a ketone group to give an S type 4-substituted hydroxypyranoindolidine compound of the formula [VII]:

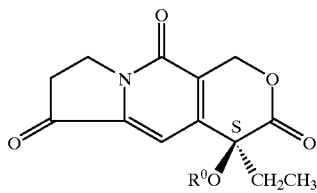

[VII]

wherein the symbol is as defined above.

The above compound [VII] is subjected to Friedlaender reaction together with an o-acylaniline compound of the formula [XIV]:

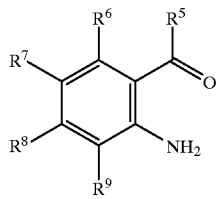

[XIV]

wherein the groups $R^5$–$R^9$ are each a hydrogen atom or a substituent being optionally protected, in a conventional manner to give a camptothecin compound having a substituent on the 20-hydroxy group of the formula [XV]:

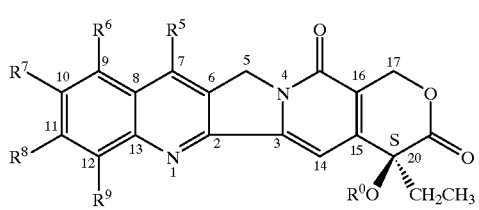

[XV]

wherein the symbols are as defined above, and the compound [XV] is subjected to removal of $R^0$ group and further, when the groups $R^5$–$R^9$ are protected, subjected to removal of the protecting group, and further optionally to conversion into a salt thereof to give a camptothecin compound of the formula [XVI]:

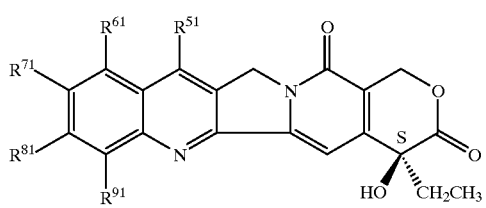

[XVI]

wherein the groups $R^{51}$–$R^{91}$ are each a hydrogen atom or an unprotected substituent, or a salt thereof.

Besides, it is assumed that in the above intramolecular cyclization reaction of the S type 2-substituted hydroxy-2-(6-substituted hydroxymethyl-indolidinyl)butyric ester compound [VI], there is produced a compound of the following formula:

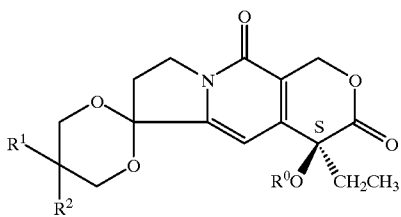

wherein the symbols are as defined above.

The camptothecin compound [XVI] or a salt thereof may also be prepared by a process comprising the following steps:

(a-1) subjecting the S type 4-substituted hydroxypyranoindolidine compound [VII] to removal of the group $R^0$, or (a-2) subjecting the S type 2-substituted hydroxy-2-(6-substituted hydroxymethylindolidinyl)butyric ester compound [VI] to an ester hydrolysis to give an S type 2-hydroxy-2-(6-hydroxymethylindolidinyl)butyric acid compound of the formula [IX]:

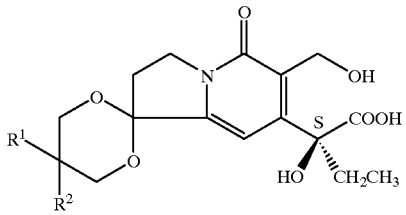

wherein the symbols are as defined above, subjecting the compound [IX] to an intramolecular cyclization reaction and thereafter or simultaneously with the cyclization reaction converting the acetal group thereof into a ketone group, and further optionally converting the product into a salt thereof to give an S type 4-hydroxypyranoindolidine compound of the formula [VIII]:

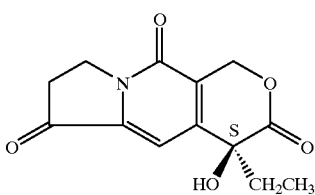

or a salt thereof, (b) subjecting the compound [VIII] to Friedlaender reaction together with an o-acylaniline compound [XIV] in a usual manner to give a camptothecin compound of the formula [XVII]:

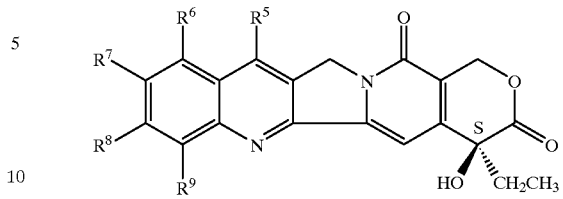

wherein the symbols are as defined above, (c) subjecting the compound [XVII] to removal of the protecting group of the groups $R^5$–$R^9$, when these groups contain a protecting group, and further (d) optionally converting the product into a salt thereof.

Alternatively, the camptothecin compound [XVI] or a salt thereof may be prepared by a process comprising the following steps:

(i) subjecting the S type 2-substituted hydroxy-2-(6-substituted hydroxymethylindolidinyl)butyric ester compound [VI] to an ester hydrolysis to give an S type 2-hydroxy-2-(6-hydroxymethylindolidinyl)butyric acid compound [IX] or a salt thereof, (ii) subjecting the compound [IX] to an intramolecular cyclization reaction and further optionally converting the product into a salt thereof to give an S type 4-hydroxypyranoindolidine compound of the formula [X]:

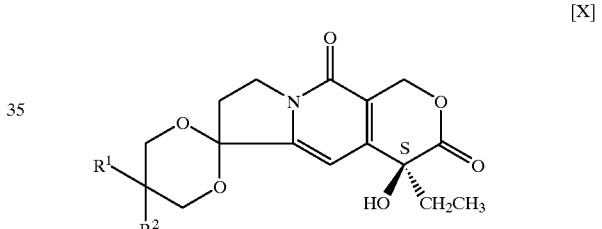

wherein the symbols are as defined above, or a salt thereof, (iii) reacting the compound [X] with a lower alkanoic acid of the formula [XI]:

$R^4OH$ [XI]

wherein $R^4$ is a lower alkanoyl group, or a reactive derivative thereof to give an S type 4-alkanoyloxypyranoindolidine compound of the formula [XII]:

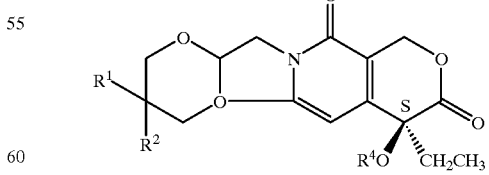

wherein the symbols are as defined above, (iv) converting the acetal group of said compound [XII] into a ketone group to give an S type 4-alkanoyloxypyranoindolidine compound of the formula [XIII]:

[XIII]

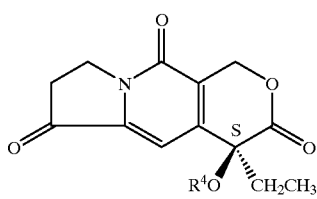

wherein the symbols are as defined above, (v) subjecting the compound [XIII] to Friedlaender reaction together with an o-acylaniline compound [XIV] in a usual manner to give a camptothecin compound having a substituent on the 20-hydroxy group of the formula [XVIII]:

[XVIII]

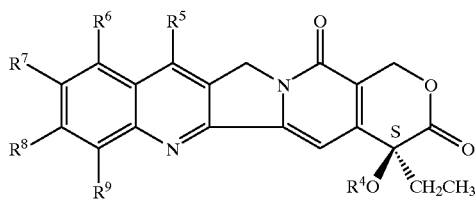

wherein the symbols are as defined above, (vi) subjecting the compound [XVIII] to removal of the group $R^4$ and further to removal of the protecting group of the groups $R^5$–$R^9$, when these groups contain a protecting group, and further (vii) optionally converting the product into a salt thereof.

In the above compounds, the groups $R^5$–$R^9$ include any substituents like in known camptothecin derivatives (cf. for example, EP-A-540099, EP-A-296597, JP-A-6-228141, WO 90/03169, EP-A-418099) as well as in the camptothecin derivatives as disclosed in European Patent Publication Nos. 757049 and 781781, for example, the following groups:

(a) the adjacent two groups among the $R^5$–$R^9$ combine to form a straight chain or branched chain alkylene group having 2 to 6 carbon atoms, or are both a hydrogen atom, and one of the remaining groups is —$Q_q$—$Alk_p$—$R^{10}$, and other two of the remaining groups are a hydrogen-atom, a substituted or unsubstituted lower alkyl group, or a halogen atom, (b) the adjacent two groups among the $R^5$–$R^9$ combine to form a straight chain or branched chain alkylene group having 2 to 6 carbon atoms, and any one carbon atom in the alkylene group is substituted by a group of the formula: —$Q_q$—$Alk_p$—$R^{10}$, and the remaining three groups of the $R^5$–$R^9$ are a hydrogen atom, a substituted or unsubstituted lower alkyl group, or a halogen atom, in the above (a) and (b), one or two methylene groups in the alkylene group may be replaced by —O—, —S— or —NH—, Q is —O— or —NH—, Alk is a straight chain or branched chain alkylene group having 1 to 6 carbon atoms, which may optionally be intervened by an oxygen atom, $R^{10}$ is a protected amino group, a protected lower alkylamino group, a protected piperazino group, or a protected hydroxy group, p and q are both 0 or 1, or when p is 1, q is 0.

The $R^{51}$–$R^{91}$ are a group derived from $R^5$–$R^9$ by removing the protecting group, specifically the groups as defined for $R^5$–$R^9$ wherein the group $R^{10}$ is a group obtained by removing the protecting group, that is, the group $R^{10}$ being an amino group, a lower alkylamino group, a piperazino group, or a hydroxy group.

Preferred combinations of the groups $R^{51}$–$R^{91}$ are as follows:

(i) $R^{71}$ is 3-aminopropyloxy, $R^{51}$ is ethyl, and $R^{61}$, $R^{81}$ and $R^{91}$ are each hydrogen atom, (ii) $R^{51}$ is piperazinomethyl, $R^{61}$ and $R^{91}$ are each hydrogen atom, and $R^{71}$ and $R^{81}$ combine to form ethylenedioxy, (iii) $R^{51}$ is aminomethyl, $R^{71}$ and $R^{81}$ combine to form ethylenedioxy, and $R^{61}$ and $R^{91}$ are each hydrogen atom, (iv) $R^{51}$ is aminomethyl, $R^{71}$ and $R^{81}$ combine to form methylenedioxy, and $R^{61}$ and $R^{91}$ are each hydrogen atom, (v) $R^{61}$ is amino, and $R^{51}$, $R^{71}$, $R^{81}$ and $R^{91}$ are each hydrogen atom, (vi) $R^{51}$ and $R^{61}$ combine to form amino-substituted trimethylene, $R^{71}$ is methyl, $R^{81}$ is fluorine atom, and $R^{91}$ is hydrogen atom, (vii) $R^{51}$ and $R^{61}$ combine to form trimethylene, $R^{71}$ is 3-aminopropyloxy, $R^{81}$ and $R^{91}$ are each hydrogen atom, (viii) $R^{71}$ is 3-aminopropyloxy, and $R^{51}$, $R^{61}$, $R^{81}$ and $R^{91}$ are each hydrogen atom.

The salt of the S type 4-hydroxypyranoindolidine compound [VIII], S type 2-hydroxy-2-(6-hydroxymethylindolidinyl)butyric acid compound [IX] or S type 4-hydroxypyranoindolidine compound [X] includes an alkali metal salt (e.g. sodium salt, lithium salt), and the salt of the camptothecin compound [XVI] includes a salt with an inorganic acid (e.g. hydrochloride, sulfate) or a salt with an organic acid (e.g. oxalate, tosylate).

In the above process for the preparation of a camptothecin compound, the reduction and alkanoylation of the S type 2-substituted hydroxy-2-indolidinylbutyric ester compound [II] are carried out in a suitable solvent. The reduction is usually carried out by using a catalyst (e.g. Raney nickel) under hydrogen atmosphere at a room temperature to 60° C. The alkanoylation is usually carried out by using a conventional alkanoylating agent (e.g. a lower alkanoic acid, a lower alkanoic halide, a lower alkanoic acid anhydride) at a room temperature to 60° C. The solvent to be used in these reactions includes a lower alkanoic acid anhydride (e.g. acetic anhydride), a lower alkanoic acid (e.g. acetic acid), or a mixture of them. When a lower alkanoic acid anhydride, a lower alkanoic acid, or a mixture of them is used in the reduction reaction, they may be used also as an alkanoylating agent, and in such a case, the reduction and the alkanoylation can proceed in a single step.

The nitrosation and rearrangement of an S type 2-substituted hydroxy-2-(6-substituted aminomethylindolidinyl)butyric ester compound [V] can be carried out by a similar method to that disclosed in Journal of Medicinal Chemistry, vol. 23, pp. 554–560 (1980) in a suitable solvent. The nitrosation is carried out under an acidic condition with a conventional nitrosating agent (e.g. sodium nitrite, potassium nitrite) at 0° C. The solvent to be used in this reaction includes a lower alkanoic acid anhydride (e.g. acetic anhydride), a lower alkanoic acid (e.g. acetic acid), or a mixture of them.

The subsequent rearrangement reaction can be carried out by heating the product obtained by the above nitrosation at a temperature of 60 to 70° C. The solvent to be used in the rearrangement reaction includes a halogenated hydrocarbon (e.g. carbon tetrachloride, chloroform, methylene chloride), an ester solvent (e.g. ethyl acetate), a non-aromatic hydrocarbon solvent (e.g. n-hexane), an aromatic hydrocarbon solvent (e.g. toluene).

The ester hydrolysis of the S type 2-substituted hydroxy-2-(6-substituted hydroxymethylindolidinyl)butyric ester compound [VI] can be carried out by a conventional method for the ester hydrolysis in a suitable solvent in the presence of a base.

The base to be used in the ester hydrolysis includes inorganic bases, such as an alkali metal hydroxide (lithium hydroxide, sodium hydroxide, potassium hydroxide), an alkaline earth metal hydroxide (e.g. calcium hydroxide), an ammonium hydroxide, an alkali metal carbonate (e.g. sodium carbonate, potassium carbonate), an alkali metal hydrogen carbonate (e.g. sodium hydrogen carbonate), organic bases, such as an alkali metal alkoxide (e.g. sodium ethoxide, sodium methoxide), an alkali metal phenoxide (e.g. sodium phenoxide), a mono-, di- or tri-lower alkylamine (e.g. methylamine, ethylamine, N,N-dimethyl-1,3-propanediamine, trimethylamine, triethylamine). The solvent includes an alcohol solvent (e.g. methanol, ethanol, propanol, isopropanol, butanol), a sulfoxide solvent (e.g. dimethylsulfoxide), a halogenated hydrocarbon solvent (e.g. methylene chloride), an ether solvent (e.g. tetrahydrofuran), or a mixture of the organic solvent with water. When the base is a liquid, it may be used also as a solvent. The reaction is preferably carried out at a temperature of 0 to 50° C., more preferably at a room temperature.

When the intramolecular cyclization reaction of an S type 2-substituted hydroxy-2-(6-substituted hydroxymethylindolydinyl)butyric ester compound [VI] or an S type 2-hydroxy-2-(6-hydroxymethylindolidinyl)butyric acid compound [IX] or a salt thereof and the conversion of the acetal group into a ketone group are carried out simultaneously, they can be carried out in a single step by treating the compound with a suitable acid. The acid includes an inorganic acid (e.g. hydrochloric acid, sulfuric acid), an organic acid (e.g. trifluoroacetic acid), and a mixture of them with water. The acid may be used also as a solvent.

On the other hand, when the intramolecular cyclization reaction of an S type 2-substituted hydroxy-2-(6-substituted hydroxymethylindolydinyl)butyric ester compound [VI] or an S type 2-hydroxy-2-(6-hydroxymethylindolidinyl)butyric acid compound [IX] or a salt thereof is first carried out and thereafter the conversion of the acetal group into a ketone group is carried out, the reactions can be carried out by treating the compound with an acid (e.g. acetic acid, citric acid) weaker than the acid used in the above single step reaction and then treating the resultant with the same stronger acid as used in the above single step reaction. For example, when the S type 2-hydroxy-2-(6-hydroxymethylindolidinyl)butyric acid compound [IX] or a salt thereof is treated with a weaker acid, there is obtained an S type 4-hydroxypyranoindolidine compound [X], which is converted into an S type 4-hydroxypyranoindolidine compound [VIII] by treating it with a stronger acid.

The reaction of an S type 4-hydroxypyranoindolidine compound [X] or a salt thereof with a lower alkanoic acid [XI] or a reactive derivative thereof can be carried out in the presence of a base.

The lower alkanoic acid [XI] includes, for example, acetic acid, and the reactive derivative thereof includes an acid anhydride (e.g. acetic anhydride), an acid halide (e.g. acetic chloride), an activated ester (e.g. p-nitrophenyl ester). The base includes an alkali metal hydride (e.g. sodium hydride, potassium hydride), an alkali metal carbonate (e.g. sodium carbonate, potassium carbonate), an alkali metal hydrogen carbonate (e.g. sodium hydrogen carbonate, potassium hydrogen carbonate), pyridine, and 4-N,N-dimethylaminopyridine. The reaction is usually carried out at a temperature of 0 to 50° C., preferably at a room temperature.

The subsequent conversion of the acetal group of an S type 4-substituted hydroxypyranoindolidine compound [XII] into a ketone group can be carried out by treating the compound with a suitable acid. The acid may be the same acid as used in case of carrying out the intramolecular cyclization reaction of an S type 2-substituted hydroxy-2-(6-substituted hydroxymethylindolidinyl)butyric acid compound [VI] or an S type 2-hydroxy-2-(6-hydroxymethylindolidinyl)butyric acid compound [IX] or a salt thereof and the conversion of the acetal group into a ketone group in a single step.

The reaction of an S type 4-substituted hydroxypyranoindolidine compound [VII], an S type 4-hydroxypyranoindolidine compound [VIII] or a salt thereof, or an S type 4-substituted hydroxypyranoindolidine compound [III] with an o-acylaniline compound [XIV] can be carried out by the known Friedlaender reaction [cf. Organic Reactions, vol. 28, pp. 37–202, John Wiley & Sons, Inc., New York (1982)].

The 4-substituted hydroxypyranoindolidine compound [VII] and 4-alkanoyloxypyranoindolidine compound [XIII] are more stable than an S type 4-hydroxypyranoindolidine compound [VIII] or a salt thereof and further are less affect on decomposition of o-acrylaniline compound [XIV] during the Friedlaender reaction and thereby can reduce the undesirable by-production of contaminating impurities, and hence, those compounds are favorably used in the reaction with less amount of the o-acylaniline compound [XIV], with simple post-reaction treatment such as purification and can give the desired camptothecin compounds [XVI] or a salt thereof in a higher yield.

Moreover, the 4-alkanoyloxypyranoindolidine compound [XIII] has a molecular weight much smaller than that of the 4-substituted hydroxypyranoindolidine compound [VII], and hence, it can be used in the Friedlaender reaction in a smaller amount with a smaller reaction vessel.

The removal of the protecting groups contained in the groups $R^5$–$R^9$ can be carried out by a conventional method suitable to the protecting groups contained therein. For example, when the amino protecting group is a benzyloxycarbonyl group, it can be removed by catalytic reduction in the presence of palladium-carbon in a suitable solvent (e.g. tetrahydrofuran, methanol), and when the amino protecting group is a tert-butoxycarbonyl group, it can be removed by treating it with an acid (e.g. hydrochloric acid, trifluoroacetic acid) in a suitable solvent (e.g. tetrahydrofuran, methanol, dioxane, methylene chloride).

The removal of the residue $R^0$ from an S type 4-substituted hydroxypyranoindolidine compound [VII] or from a camptothecin compound having 20-substituted hydroxy group [XV] can be carried out by a conventional ester hydrolysis in the presence of a base in a suitable solvent. The base and solvent are the same as those used in the ester hydrolysis of an S type 2-substituted hydroxy-2-(6-substituted hydroxymethylindolidinyl)butyric ester compound [VI]. The reaction may be carried out under cooling, at a room temperature, or with heating.

Besides, the removal of the group $R^4$ from the camptothecin compound having 20-alkanoylated hydroxy group [XVIII] can be carried out in the same manner as in the ester hydrolysis of an S type 2-substituted hydroxy-2-(6-substituted hydroxymethylindolidinyl)butyric ester compound [VI] or in the removal of the residue $R^0$ from an S type 4-substituted hydroxypyranoindolidine compound [VII] or from a camptothecin compound having 20-substituted hydroxy group [XV].

The o-acylaniline compound [XIV] to be used in the above condensation reactions can be prepared by a process as shown in the following reaction scheme-1:

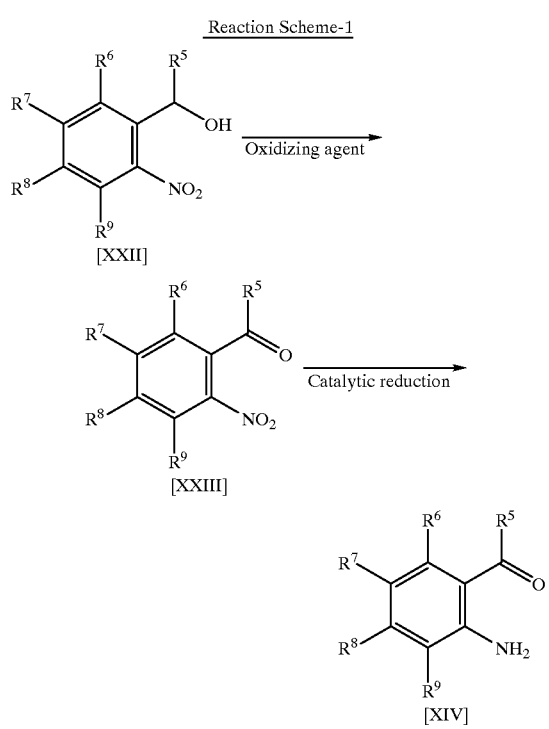

wherein the symbols are as defined above.

That is, a hydroxyl compound [XXII] is treated with an oxidizing agent (e.g. activated manganese dioxide, pyridinium dichromate) to give a ketone compound [XXIII], followed by subjecting it to a catalytic reduction in the presence of a suitable catalyst (e.g. palladium-carbon) in a suitable solvent to give the desired o-acylaniline compound [XIV]. Moreover, when the protecting group(s) in $R^5$–$R^9$ is/are removed by a catalytic reduction, the product may be again introduced with a protecting group to give an o-acylaniline compound [XIV]. Besides, an o-acylaniline compound [XIV] wherein $R^5$ is a lower alkyl group may also be prepared by treating a hydroxyl compound [XXII] wherein $R^5$ is a lower alkenyl group with an oxidizing agent, followed by catalytic reduction.

Furthermore, the hydroxyl compound [XXII] wherein the groups $R^5$–$R^9$ have a protected amino group, a protected lower alkylamino group, a protected piperazino group, or a protected hydroxy group may also be prepared by introducing a protecting group to the corresponding compound having unprotected group(s) by a conventional method.

The 2-halo-2-indolidinylacetic ester compound [III] used in the present invention is novel and can be prepared by a process as shown in the following reaction scheme-2.

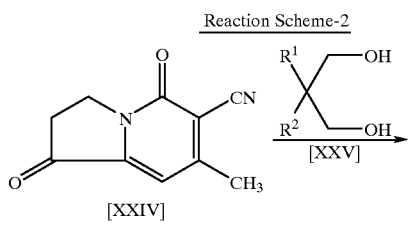

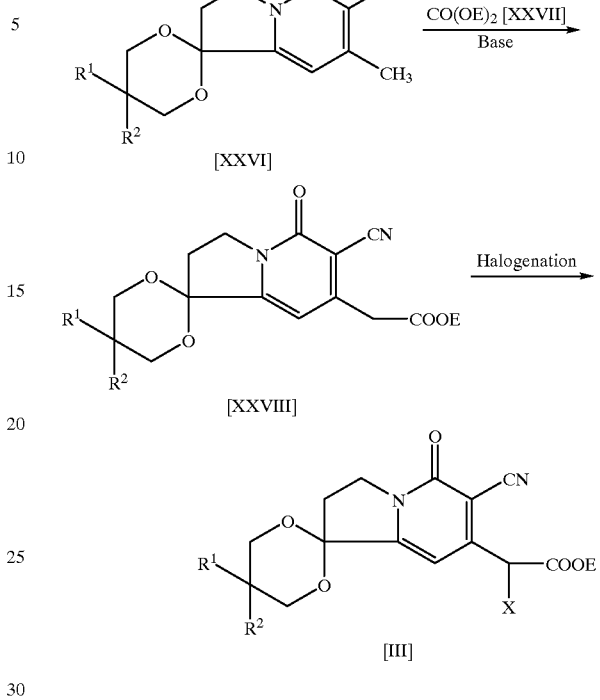

wherein the symbols are as defined above.

That is, an indolidine compound [XXIV] is reacted with a 1,3-propane-diol compound [XXV] in the presence of an acid (e.g. p-toluenesulfonic acid) or a Lewis acid (e.g. trimethylsilyl chloride) to give an indolidinylmethane compound [XXVI], and the compound [XXVI] is treated with a carboxylic diester [XXVII] in the presence of a base (e.g. sodium hydride, potassium t-butoxide) in a suitable solvent (e.g. toluene, tetrahydrofuran) to give a 2-indolidinylacetic ester compound [XXVIII], which is further halogenated by a conventional method to give the desired 2-halo-2-indolidinylacetic ester compound [III].

Among the R type nitrogen-containing fused heterocyclic carboxylic acid compounds [IV] or a salt thereof, the nitrogen-containing fused heterocyclic carboxylic acid compound [XIX] or a salt thereof is novel and can be prepared by reacting an N-unsubstituted nitrogen-containing fused heterocyclic carboxylic acid compound of the formula [XXIX]:

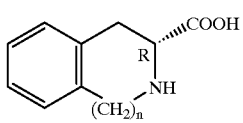

wherein the symbols are as defined above, or a salt thereof with a sulfonic acid of the formula [XXX]:

wherein the symbol is as defined above, or a reactive derivative or salt thereof by a conventional sulfonamide forming reaction, for example, by reacting a nitrogen-containing fused heterocyclic carboxylic acid compound [XXIX] and a halide (e.g. chloride) of a sulfonic acid [XXX] in the presence of a base (e.g. alkali metal hydroxide).

In the present description and claims, the term "S type" means that the absolute configuration at 2-position of a 2-substituted hydroxy-2-indolidinylbutyric ester compound [II], a 2-substituted hydroxy-2-(6-substituted aminomethylindolidinyl)butyric ester compound [V], a 2-substituted hydroxy-2-(6-substituted hydroxymethylindolidinyl)butyric ester compound [VI] or a 2-hydroxy-2-(6-hydroxymethylindolidinyl)butyric acid compound [IX] or a salt thereof, or the absolute configuration at 4-position of a 4-substituted hydroxypyranoindolidine compound [VII], a 4-hydroxypyranoindolidine compound [VIII] or a salt thereof, a 4-hydroxypyranoindolidine compound [X] or a salt thereof, a 4-alkanoyloxypyranoindolidine compound [XII], or a 4-alkanoyloxypyranoindolidine compound [XIII]; and the absolute configuration at 2-position of a 2-[(R)-N-tosylprolyloxy]-2-indolidinylbutyric ester compound [XXI] are all in "S" configuration.

Throughout the present description and claims, the term "lower alkyl" means a straight chain or branched chain alkyl group having 1 to 6 carbon atoms, the term "lower alkanoyl group" and "lower alkanoic acid" mean a straight chain or branched chain alkanoyl group and alkanoic acid which have each 1 to 7 carbon atoms, respectively. The term "alkylene group" means a straight chain or branched chain alkylene group having 1 to 10 carbon atoms.

EXAMPLES

This invention is illustrated in more specifically by the following examples and reference examples but should not be construed to be limited thereto.

Example 1

(1) A mixture of ethyl 2-bromo-2-[6-cyano-1,1-(2,2-dimethyl-trimethylenedioxy)-5-oxo-1,2,3,5-tetrahydro-7-indolidinyl]acetate (22.21 g), (3R)-N-(4-biphenylylsulfonyl)-1,2,3,4-tetrahydro-3-isoquinolinecarboxylic acid (24.70 g) and potassium carbonate (5.11 g) in dimethylformamide (220 ml) is stirred at 60° C. for 70 minutes. The reaction mixture is extracted with ethyl acetate, and the extract is washed with a saturated aqueous saline solution and dried over sodium sulfate. After distilling off the solvent under reduced pressure, the residue is purified with a silica gel column chromatography (eluent; chloroform : ethyl acetate=10:1→6:1) to give ethyl 2-[[(3R)-N-(4-biphenyl-ylsulfonyl)-1,2,3,4-tetrahydro-3-isoquinolyl]carbonyloxy] -2-[6-cyano-1,1-(2,2-dimethyltrimethylenedioxy)-5-oxo-1,2,3,5-tetrahydro-7-indolidinyl]acetate (35.41 g) as colorless powders.
Yield: 92%

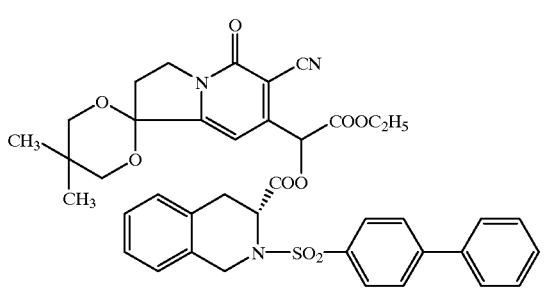

IR (Nujol, cm$^{-1}$): 2220, 1750, 1665, 1615
MS (m/z): 738 (MH$^+$)
NMR (300 MHz, CDCl$_3$, δ): 0.89 and 0.90 (3H, s), 1.10 and 1.15 (3H, t, J=7 Hz), 1.33 and 1.35 (3H, s), 2.45–2.60 (2H, m), 3.25–3.40 (2H, m), 3.61–3.76 (4H, m), 3.95–4.22 (4H, m), 4.58 and 4.68 (1H, d, J=16 Hz), 4.72 and 4.75 (1H, d, J=16 Hz), 5.22 and 5.29 (1H, dd and t, J=3.6 and 5Hz), 6.01 and 6.04 (1H, s), 6.58 and 6.65 (1H, s), 7.02–7.20 (4H, m), 7.37–7.51 (3H, m), 7.54–7.60 (2H, m), 7.62–7.68 (2H, m), 7.85–7.93 (2H, m)

(2) Ethyl 2-[[(3R)-N-(4-biphenylylsulfonyl)-1,2,3,4-tetrahydro-3-isoquinolyl]carbonyloxy]-2-[6-cyano-1,1-(2,2-dimethyltrimethylenedioxy)-5-oxo-1,2,3,5-tetrahydro-7-indolidinyl]acetate (33.63 g) is dissolved in dry dimethylacetamide-toluene (1:1) (330 ml), and thereto is added a 60% oily dispersion of sodium hydride (2.21 g) (1.2 equivalent), and the mixture is stirred at room temperature for 75 minutes. To the mixture is added ethyl iodide (36.5 ml) (10 equivalents), and the mixture is further stirred at room temperature overnight. The reaction mixture is extracted with ethyl acetate, and the extract is washed with an aqueous citric acid solution and an aqueous saturated saline solution, dried over sodium sulfate-magnesium sulfate, and then treated with active carbon (5 g). After distilling off the solvent under reduced pressure, the residue (35.69 g) [the diastereoselectivity of 2S compound and 2R compound=15.2:1.0 (88% d.e.) which is calculated based on the ratio of integral value at the peak of δ:6.71 and 6.46 in NMR spectrum] is dissolved in acetone (60 ml), and the mixture is stirred at room temperature, and thereto added portionwise hexane (76 ml) and also added a seed crystal of the desired diastereomer. The precipitated crystals are collected by filtration, washed with acetone-hexane (60:76) (about 100 ml) to give ethyl (2S)-2-[[(3R)-N-(4-biphenylylsulfonyl)-1,2,3,4-tetrahydro-3-isoquinolyl] carbonyloxy]-2-[6-cyano-1,1-(2,2-dimethyltrimethylenedioxy)-5-oxo-1,2,3,5-tetrahydro-7-indolidinyl]butyrate (26.64 g) as colorless crystals.
Yield: 76%

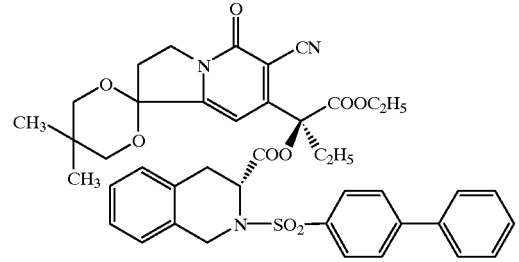

m.p.: >82° C. (gradually decomposed)
[α]$_D^{26}$:−43.3° (c=1.02, chloroform)
IR (Nujol, cm$^{-1}$): 2220, 1755, 1660, 1615
MS (m/z): 766 (MH$^+$)
NMR (300 MHz, CDCl$_3$, δ): 0.70 (3H, t, J=7.5 Hz), 0.85 (3H, brs), 1.02 (3H, t, J=7 Hz), 1.21 (3H, brs), 2.16–2.55 (4H, m), 3.35 (1H, dd, J=6.5 and 16 Hz), 3.50 (1H, dd, J=3 and 16 Hz), 3.55–3.70 (4H, m), 3.70–3.90 (2H, m), 3.93–4.16 (2H, m), 4.68 (1H, d, J=16Hz), 4.76 (1H, d, J=16Hz), 5.37 (1H, dd, J=3 and 6.5Hz), 6.71. (1H, s), 7.02–7.10 (1H, in), 7.10–7.20 (3H, in), 7.36–7.50 (3H, m), 7.54–7.59 (2H, m), 7.63–7.68 (2H, m), 7.89–7.96 (2H, m)

(3) Ethyl (2S)-2-[[(3R)-N-(4-biphenylylsulfonyl)-1,2,3,4-tetrahydro-3-isoquinolyl]carbonyloxy]-2-[6-cyano-1,1-(2,2-dimethyltrimethylenedioxy)-5-oxo-1,2,3,5-tetrahydro-7-indolidinyl]butyrate (23.71 g) and Raney nickel (W-4) (49 g) are dissolved in acetic anhydride-acetic acid (460 ml–190 ml), and the mixture is stirred under hydrogen atmosphere at 50–60° C. After completion of the reaction, the catalyst is filtered off, and the filtrate is concentrated under reduced pressure, and the residue is purified with a silica gel column chromatography (eluent; chloroform: methanol= 100:1→70:1→60:1) to give ethyl (2S)-2-[[(3R)-N-(4- biphenylylsulfonyl)-1,2,3,4-tetrahydro-3-isoquinolyl]-carbonyloxy]-2-[6-[(acetylamino)methyl]-1,1-(2,2-dimethyltrimethylenedioxy)-5-oxo-1,2,3,5-tetrahydro-7-indolidinyl]butyrate (22.10 g) as pale yellow powders.
Yield: 87%

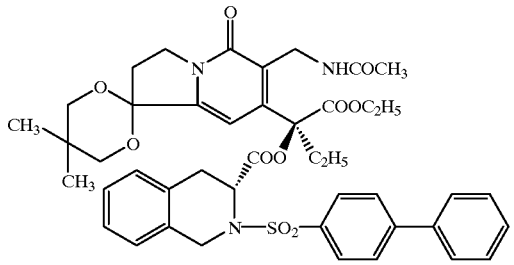

$[\alpha]_D^{26}$: −14.9° (c=1.01, chloroform)
IR (Nujol, cm$^{-1}$): 3405, 3295, 1750, 1660
MS (m/z): 812 (MH$^+$)
NMR (300 MHz, CDCl$_3$, δ): 0.69 (3H, t, J=7.5Hz), 0.88 (3H, s), 1.02 (3H, t, J=7 Hz), 1.24 (3H, s), 1.96 (3H, s), 2.12–2.55 (4H, m), 3.31 (1H, dd, J=6.5 and 16 Hz), 3.41 (1H, dd, J=3 and 16 Hz), 3.59 (2H, s), 3.63 (2H, s), 3.84 (1H, dq, J=11 and 7 Hz), 3.94–4.14 (3H, m), 4.54 (1H, dd, J=14 and 5.5 Hz), 4.58–4.68 (1H, m), 4.63 (1H, d, J=15 Hz), 4.71 (1H, d, J=15 Hz), 5.25 (1H, dd, J=3 and 6.5 Hz), 6.74 (1H, s), 7.00–7.19 (5H, m), 7.37–7.50 (3H, m), 7.54–7.64 (4H, m), 7.83–7.89 (2H, m)

(4) Ethyl (2S)-2-[[(3R)-N-(4-biphenylylsulfonyl)-1,2,3,4-tetrahydro-3-isoquinolyl]carbonyloxy]-2-[6-[(acetylamino)methyl]-1,1 -(2,2-dimethyltrimethylenedioxy)-5-oxo-1,2,3,5-tetrahydro-7-indolidinyl]butyrate (30.16 g) is dissolved in acetic anhydride-acetic acid (450 ml–150 ml), and thereto is added sodium nitrite (13.18 g) under ice cooling, and the mixture is stirred on an ice-water bath for 4 hours. The reaction mixture is poured onto chloroform (1.5 liter), and undissolved substances are filtered off. The filtrate is evaporated to dryness under reduced pressure, and the residue is mixed with ethyl acetate (900 ml), and the mixture is stirred at 60° for 13 hours. The reaction mixture is diluted with ethyl acetate (700 ml), and the mixture is washed with water and saline solution, dried over sodium sulfate and then treated with active carbon. After distilling off the solvent under reduced pressure, the residue is crystallized from ethyl acetate-hexane to give ethyl (2S)-2-[[(3R)-N-(4-biphenylylsulfonyl)-1,2,3,4-tetrahydro-3-isoquinolyl]carbonyloxy]-2-[6-acetoxymethyl-1,1-(2,2-dimethyltrimethylenedioxy)-5-oxo-1,2,3,5-tetrahydro-7-indolidinyl]butyrate (16.77 g) as colorless prisms.
Yield: 55%

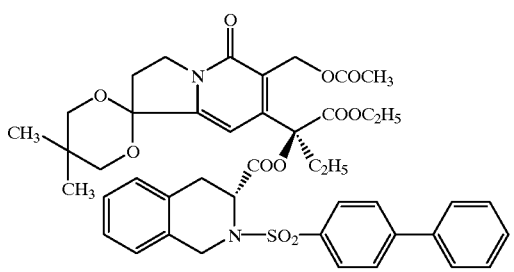

m.p.: 145–148° C.
$[\alpha]_D^{27}$: −9.6° (c=1.0, chloroform)
IR (Nujol, cm$^{-1}$): 1755, 1659, 1614
MS (m/z): 813 (MH$^+$)
NMR (300 MHz, CDCl$_3$, δ): 0.54 (3H, t, J=7.4 Hz), 0.88 (3H, s), 1.08 (3H, t, J=7.1 Hz), 1.30 (3H, s), 2.09 (3H, s), 2.24 (2H, q like, J=7.6 Hz), 2.47 (2H, t, J=7 Hz), 3.27 (2H, m), 3.65 (4H, m), 3.91–4.17 (4H, m), 4.64 (1H, d, J=15.6 Hz), 4.72 (1H, d, J=15.6 Hz), 5.13 (1H, dd, J=5.3 and 3 Hz), 5.25 (2H, s), 6.65 (1H, s), 7.01–7.20 (4H, m), 7.37–7.50 (3H, m), 7.55–7.59 (2H, m), 7.65 (2H, d like, J=8.6 Hz), 7.90 (2H, d like, J=8.6 Hz)

(5) Ethyl (2S)-2-[[(3R)-N-(4-biphenylylsulfonyl)-1,2,3,4-tetrahydro-3-isoquinolyl]carbonyloxy]-2-[6-acetoxymethyl-1,1-(2,2-dimethyltrimethylenedioxy)-5-oxo-1,2,3,5-tetrahydro-7-indolidinyl]butyrate (1.457 g) is dissolved in a 80% aqueous trifluoroacetic acid solution (15 ml) under ice cooling, and the mixture is stirred at room temperature for 2 days. The reaction mixture is concentrated under reduced pressure, and the residue is extracted with chloroform, and the extract is washed with water, and dried over magnesium sulfate. The extract is distilled to remove the solvent under reduced pressure to give (4S)-7,8-dihydro-4-ethyl-4-[[(3R)-N-(4-biphenylylsulfonyl)-1,2,3,4-tetrahydro-3-isoquinolyl]carbonyloxy]-1H-pyrano[3,4-f]indolidine-3,6,10(4H)-trione (1.145 g) as colorless foam.
Yield: 100%

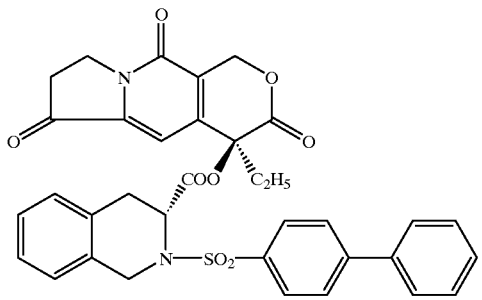

IR (Nujol, cm$^{-1}$): 1746,1661
MS (m/z): 639 (MH$^+$)
NMR (300 MHz, CDCl$_3$, δ): 0.82 (3H, t, J=7.5 Hz), 1.78–2.09 (4H, m), 2.66–2.90 (2H, m), 3.23 (2H, d like, J=4.6 Hz), 4.07–4.27 (2H, m), 4.53 (1H, d, J=15.4 Hz), 4.69 (1H, d, J=15.6 Hz), 5.01 (1H, t, J=5.2 Hz), 5.23 (1H, d, J=18 Hz), 5.49 (1H, d, J=17.9 Hz), 6.58 (1H, s), 7.01–7.18 (4H, m), 7.38–7.56 (5H, m), 7.62 (2H, dlike, J=8.6 Hz), 7.89 (2H, d like, J=8.6 Hz)

(6) (4S)-7,8-Dihydro-4-ethyl-4-[[(3R)-N-(4-biphenylylsulfonyl)-1,2,3,4-tetrahydro-3-isoquinolyl]carbonyloxy]-1H-pyrano[3,4-f]indolidine-3,6,10(4H)-trione (1.145 g) and 1-[5'-(3"-(t-butoxycarbonylaminopropyloxy)-2'-aminophenyl]propan-1-one (867 mg) are dissolved in acetic acid (15 ml), and the mixture is stirred at 60° C. for 47 hours. The reaction mixture is concentrated under reduced pressure, and the resulting crude product is purified with a silica gel column chromatography (eluent; chloroform: ethyl acetate= 2:1→1:1) and then recrystallized from ethyl acetate-hexane to give (20S)-7-ethyl-10-[3-(tert-butoxycarbonylamino)propyloxy]-20-O-[[(3R)-N-(4-biphenylylsulfonyl)-1,2,3,4-tetrahydro-3-isoquinolyl]carbonyl]camptothecin (1.11 g) as colorless crystals.
Yield: 67%

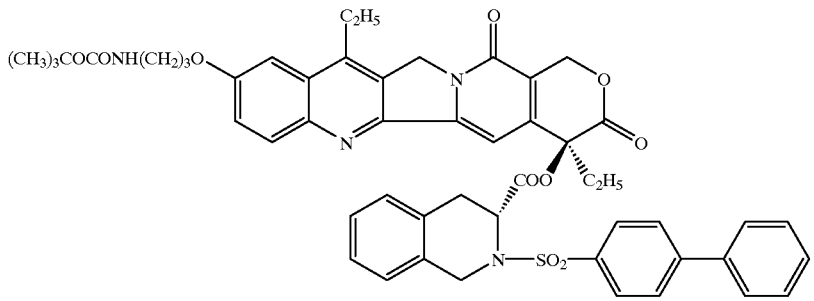

m.p.: 213–216° C.
IR (Nujol, cm$^{-1}$): 3407, 1763, 1753, 1709, 1669, 1614
MS (m/z): 925 (MH$^+$)
NMR (300 MHz, CDCl$_3$, δ): 0.86 (3H, t, J=7.5 Hz), 1.35 (3H, t, J=7.6 Hz), 1.46 (9H, s), 1.88–2.18 (4H, m), 2.94–3.20 (2H, m), 3.34 (2H, d, J=4.8 Hz), 3.42 (2H, q like, J=6.4 Hz), 4.22 (2H, t, J=6 Hz), 4.57 (1H, d, J=15.4 Hz), 4.73–4.81 (1H, br), 4.81 (1H, d, J=15.4 Hz), 4.90 (1H, d, J=18.7 Hz), 5.09 (1H, d, J=18.7 Hz), 5.21 (1H, d, J=4.8 Hz), 5.26 (1H, d, J=17.2 Hz), 5.51 (1H, d, J=17.2 Hz), 6.99 (1H, s), 7.01–7.18 (4H, m), 7.22–7.29 (2H, m), 7.30–7.42 (6H, m), 7.49 (1H, dd, J=9.3 and 2.7 Hz), 7.89 (2H, d like, J=8.6 Hz), 8.20 (1H, d, J=9.2 Hz) (7) (20S)-7-Ethyl-10-[3-(tert-butoxycarbonylamino)propyloxy]-20-O-[[(3R)-N-(4-biphenylylsulfonyl)-1,2,3,4-tetrahydro-3-isoquinolyl]carbonyl]-camptothecin (991 mg) is dissolved in water-methanol (6 ml–30 ml), and thereto is added lithium hydroxide monohydrate (180 mg) under ice cooling, and the mixture is stirred at room temperature for 22 hours and further stirred at 50° C. for 4 hours. The reaction mixture is concentrated under reduced pressure, and thereto are added chloroform (20 ml) and acetic acid (4 ml), and the mixture is stirred at room temperature for 19 hours. The reaction mixture is diluted with chloroform and water, and the chloroform layer is washed with water and an aqueous saturated saline solution, dried over sodium sulfate. The solvent is distilled off under reduced pressure to give (20S)-7-ethyl-10-[3-(tert-butoxycarbonylamino)propyloxy] camptothecin.

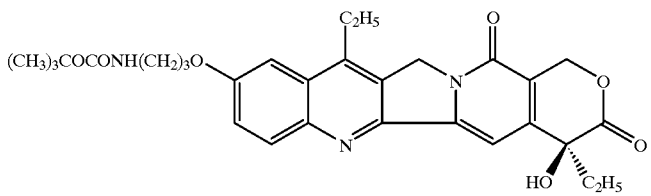

(8) The obtained (20S)-7-ethyl-10-[3-(tert-butoxycarbonylamino)propyloxy]camptothecin is dissolved in water-ethanol (5 ml - 15 ml) and thereto is added 6.6N hydrochloric acid-ethanol (5 ml), and the mixture is stirred at room temperature for 23 hours. The reaction mixture is evaporated to dryness under reduced pressure and the residue is dissolved in ethyl acetate and water. The ethyl acetate layer is further extracted with water, and the aqueous layers are combined and evaporated to dryness under reduced pressure. The residue is crystallized from isopropanol-water to give (20S)-7-ethyl-10-(3-aminopropyloxy)camptothecin hydrochloride (240 mg) as pale yellow needles.

Yield: 44% overall in the above (7) and (8)

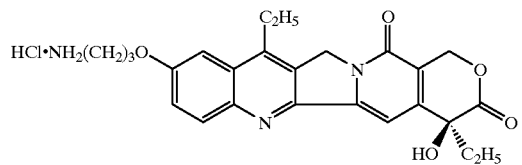

m.p.: >218° C. (decomposed)
[α]$_D^{25}$:+9.8° (c=1.0, water)
MS (m/z): 450 (M-Cl$^+$)
IR (Nujol, cm$^{-1}$): 3450, 3370, 1745, 1660
NMR (300 MHz, DMSO-d$_6$, δ): 0.88 (3H, t, J=7 Hz), 1.32 (3H, t, J=8 Hz), 1.78–1.95 (2H, m), 2.08–2.19 (2H, m), 3.0–3.1 (2H, m), 3.13–3.25 (2H, m), 4.32 (2H, t, J=6 Hz), 5.32 (2H, s), 5.43 (2H, s), 7.28 (1H, s), 7.50–7.56 (2H, m), 7.99 (3H, brs), 8.11 (1H, d, J=10 Hz)

Example 2

(1) The (4S)-7,8-dihydro-4-ethyl-4-[[(3R)-N-(4-biphenylylsulfonyl)-1,2,3,4-tetrahydro-3-isoquinolyl]carbonyloxy]-1H-pyrano[3,4-f]indolidine-3,6,10(4H)-trione obtained in Example 1-(5) is treated in the same manner as described in Example 1-(7) to give (4S)-7,8-dihydro-4-ethyl-4-hydroxy-1H-pyrano[3,4-f]indolidine-3,6,10(4H)-trione.

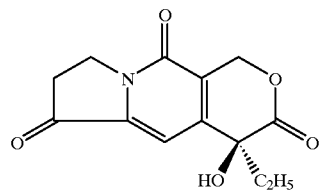

(2) The (4S)-7,8-dihydro-4-ethyl-4-hydroxy-1H-pyrano[3,4-f]indolidine-3,6,10(4H)-trione is treated in the same manner as described in Example 1-(6) and -(8) to give (20S)-7-ethyl-10-[3-aminopropyloxy)camptothecin hydrochloride as yellow powder.

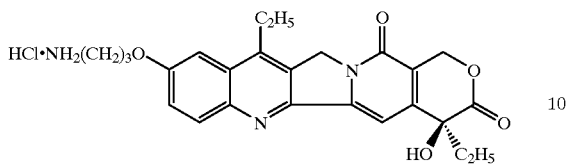

Example 3

(1) Ethyl 2-bromo-2-[6-cyano-1,1-(2,2-dimethyltrimethylenedioxy)-5-oxo-1,2,3,5-tetrahydro-7-indolidinyl]acetate (1.28 g), (3R)-N-(4-nitrophenylsulfonyl)-1,2,3,4-tetrahydro-3-isoquinolinecarboxylic acid (1.63 g) and potassium carbonate (357 mg) are mixed in dimethylformamide (15 ml), and the mixture is stirred at 70° C. for 20 minutes. The reaction mixture is treated in the same manner as described in Example 1-(1) to give ethyl 2-[[(3R)-N-(4-nitrophenylsulfonyl)-1,2,3,4-tetrahydro-3-isoquinolyl]carbonyloxy]-2-[6-cyano-1,1-(2,2-dimethyltrimethylenedioxy)-5-oxo-1,2,3,5-tetrahydro-7-indolidinyl] acetate (2.10 g) as colorless powders.
Yield: 99%

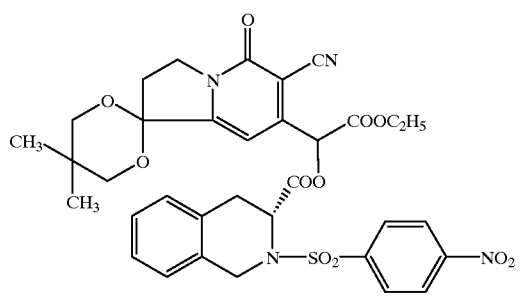

IR (Nujol, cm$^{-1}$): 2225, 1750, 1665, 1615
MS (m/z): 707 (MH$^+$)
NMR (300 MHz, CDCl$_3$, δ): 0.89 and 0.90 (3H, s), 1.10 and 1.20 (3H, t, J=7 Hz), 1.33 and 1.36 (3H, s), 2.54–2.63 (2H, m), 3.30–3.42 (2H, m), 3.60–3.75 (4H, m), 4.00–4.22 (4H, m), 4.50 and 4.57 (1H, d, J=15 Hz), 4.78 and 4.83 (1H, d, J=15 Hz), 5.22 and 5.32 (1H, dd, J=3 and 6 Hz), 5.90 and 5.95 (1H, s), 6.48 and 6.54 (1H, s), 7.00–7.23 (4H, m), 8.01 and 8.05 (2H, d, J=9 Hz), 8.29 and 8.31 (2H, d, J=9 Hz)

(2) Ethyl 2-[[(3R)-N-(4-nitrophenylsulfonyl)-1,2,3,4-tetrahydro-3-isoquinolyl]carbonyloxy]-2-[6-cyano-1,1-(2,2-dimethyltrimethylenedioxy)-5-oxo-1,2,3,5-tetrahydro-7-indolidinyl]acetate (25.09 g) is dissolved in dry dimethylacetamide-toluene (1:1) (240 ml), and the mixture is reacted in the same manner as described in Example 1-(2) by using a 60% oily dispersion of sodium hydride (1680 mg) (1.2 equivalent) and ethyl iodide (54.58 g) (10 equivalents), and the extract is washed with an aqueous citric acid solution and an aqueous saturated saline solution, dried over magnesium sulfate. After distilling off the solvent under reduced pressure, the residue is powdered from ethyl acetate - diethyl ether to give ethyl 2-[[(3R)-N-(4-nitrophenylsulfonyl)-1,2,3,4-tetrahydro-3-isoquinolyl]carbonyloxy]-2-[6-cyano-1,1-(2,2-dimethyltrimethylenedioxy)-5-oxo-1,2,3,5-tetrahydro-7-indolidinyl]butyrate (diastereomer mixture) (22.04 g) as colorless powders. The diastereoselectivity of 2S compound and 2R compound=20.0:1.0 (90% d.e.) which is calculated based on the ratio of integral value at the peak of δ:6.85 and 6.41 in NMR spectrum. The colorless powders are recrystallized from isopropanol to give a pure product (19.32 g) as colorless crystals.
Yield: 75%

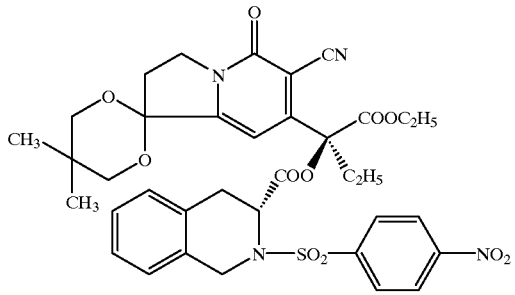

m.p.:181–182° C.
[α]$_D^{26}$:–128.39° (c=0.5, chloroform)
IR (Nujol, cm$^{-1}$): 2217, 1755, 1665, 1615
MS (m/z): 735 (MH$^+$)
NMR (300 MHz, CDCl$_3$, δ): 0.77 (3H, t, J=7.5 Hz), 0.85 (3H, s), 0.89 (3H, t, J=7 Hz), 1.20 (3H, s), 2.13 (1H, dq, J=7.3 and 15 Hz), 2.27 (1H, dq, J=7.3 and 15 Hz), 2.52–2.57 (2H, m), 3.45–3.66 (7H, m), 3.80–3.90 (1H, m), 4.16 (1H; dq, J=7.3 and 13 Hz), 4.36 (1H, dq, J=7.3 and 13 Hz), 4.52 (1H, d, J=15 Hz), 4.87 (1H, d, J=15 Hz), 5.48 (1H, dd, J=3 and 6 Hz), 6.85 (1H, s), 7.00–7.10 (1H, m), 7.12–7.23 (3H, m), 8.05 (2H, d, J=9 Hz), 8.24 (2H, d, J=9 Hz)

(3) The compound obtained in the above (2) is treated in the same manner as described in Example 1-(3)-(8) or in Example 1-(3)-(5), (7), (6) and (8) to give (20S)-7-ethyl-10-($^3$-aminopropyloxy)camptothecin hydrochloride.

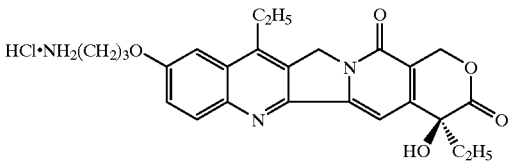

Example 4

(1) Ethyl 2-bromo-2-[6-cyano-1,1-(2,2-diethyltrimethylenedioxy)-5-oxo-1,2,3,5-tetrahydro-7-indolidinyl]acetate (363 mg), (3R)-N-(4-biphenylylsulfonyl)-1,2,3,4-tetrahydro-3-isoquinolinecarboxylic acid (472 mg) and potassium carbonate (95 mg) are mixed in dimethylformamide (4 ml), and the mixture is stirred at 70° C. for 40 minutes. The reaction mixture is treated in the same manner as described in Example 1-(1) to give ethyl 2-[[(3R)-N-(4-biphenylylsulfonyl)-1,2,3,4-tetrahydro-3-isoquinolyl]carbonyloxy]-2-[6-cyano-1,1-(2,2-diethyltrimethylenedioxy)-5-oxo-1,2,3,5-tetrahydro-7-indolidinyl]acetate (579 mg) as colorless powders.
Yield=94%

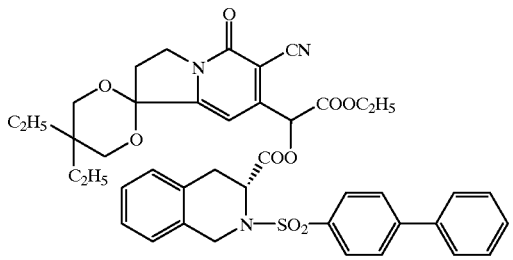

IR (Nujol, cm$^{-1}$): 2225, 1750, 1665, 1615
MS (m/z): 766 (MH$^+$)
NMR (300 MHz, CDCl$_3$, δ): 0.84 (3H, t, J=7.5 Hz), 0.94 (3H, t, J=7.5 Hz), 1.11 and 1.16 (3H, t, J=7 Hz), 1.20–1.30 (2H, m), 1.77–1.86 (2H, m), 2.45–2.60 (2H, m), 3.27–3.40 (2H, m), 3.60–3.65 (2H, m), 3.75–3.90 (2H, m), 4.00–4.20 (4H, m), 4.55 and 4.80 (2H, m), 5.21 and 5.28 (1H, dd, J=3 and 6 Hz), 6.02 and 6.06 (1H, s), 6.57 and 6.63 (1H, s), 7.00–7.20 (4H, m), 7.40–7.70 (7H, m), 7.88 and 7.90 (2H, d, J=8 Hz)

(2) Ethyl 2-[[(3R)-N-(4-biphenylylsulfonyl)-1,2,3,4-tetrahydro-3-isoquinolyl]carbonyloxy] -2-[6-cyano-1,1-(2,2-diethyltrimethylenedioxy)-5-oxo-1,2,3,5-tetrahydro-7-indolidinyl]acetate (564 mg) is dissolved in dry dimethylformamide (5 ml), and the mixture is reacted in the same manner as described in Example 1-(2) by using a 60% oily dispersion of sodium hydride (35 mg) (1.2 equivalent) and ethyl iodide (1150 mg) (10 equivalents) to give ethyl 2-[[(3R)-N-(4-bhenylylsulfonyl)-1,2,3,4-tetrahydro-3-isoquinolyl]carbonyloxy]-2-[6-cyano-1,1-(2,2-diethyltrimethylenedioxy)-5-oxo-1,2,3,5-tetrahydro-7-indolidinyl]butyrate (diastereomer mixture) (522 mg) as colorless powders. The diastereoselectivity of 2S compound and 2R compound=10.8:1.0 (83% d.e.) which is calculated based on the ratio of integral value at the peak of δ:6.67 and 6.43 in NMR spectrum.

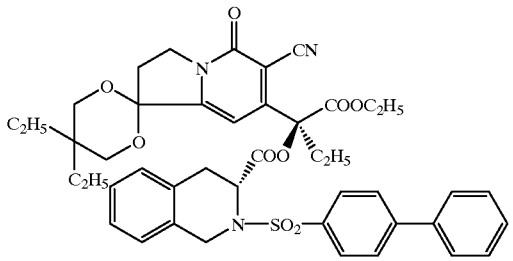

IR (Nujol, cm$^{-1}$): 2220, 1750, 1660, 1615
MS (m/z): 794 (MH$^+$)
NMR (300 MHz, CDCl$_3$, δ): 0.69 (3H, t, J=7.5 Hz), 0.81 (3H, t, J=7.5 Hz), 0.87 (3H, t, J=7.5 Hz), 1.03 (3H, t, J=7 Hz), 1.22 (2H, q, J=7.5 Hz), 1.67 (2H, q, J=7.5 Hz), 2.20–2.45 (4H, m), 3.34 (1H, dd, J=6.5 and 16 Hz), 3.48–3.58 (3H, m), 3.70–3.85 (4H, m), 3.98–4.10 (2H, m), 4.67 (1H, d, J=15 Hz), 4.76 (1H, d, J=15 Hz), 5.36 (1H, dd, J=3 and 6.5 Hz), 6.43 and 6.67 (1H, s), 7.00–7.20 (4H, m), 7.40–7.50 (3H, m), 7.56 (2H, d, J=8 Hz), 7.65 (2H, d, J=9 Hz), 7.92 (2H, d, J=9 Hz)

(3) The compound obtained in the above (2) is treated in the same manner as described in Example 1-(3)–(8) or in Example 1-(3)–(5), (7), (6) and (8) to give (20S)-7-ethyl-10-(3-aninopropyloxy)camptothecin hydrochloride.

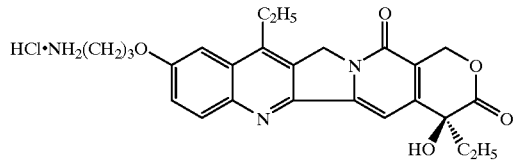

Example 5

(1) Ethyl (2S)-2-[[(3R)-N-(4-biphenylylsulfonyl)-1,2,3,4-tetrahydro-3-isoquinolyl]carbonyloxy]-2-[6-acetoxymethyl-1,1-(2,2-dimethyltrimethylenedioxy)-5-oxo-1,2,3,5-tetrahydro-7-indolidinyl]butyrate obtained in Example 1-(4) (1.00 g) is dissolved in water-methanol-tetrahydrofuran (5 ml+20 ml+5 ml), and thereto is added lithium hydroxide monohydrate (265 mg), and the mixture is stirred at room temperature for one hour to give lithium (2S)-2-hydroxy-2-[6-hydroxymethyl-1,1-(2,2-dimethyltrimethylenedioxy)-5-oxo-1,2,3,5-tetrahydro-7-indolidinyl]butyrate.

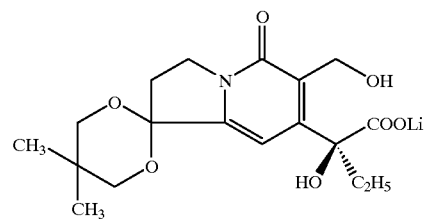

(2) Lithium (2S)-2-hydroxy-2-[6-hydroxymethyl-1,1-(2,2-dimethyltrimethylenedioxy)-5-oxo-1,2,3,5-tetrahydro-7-indolidinyl]butyrate obtained above is dissolved in chloroform (20 ml) and acetic acid (4 ml), and the mixture is stirred at room temperature for 16 hours, and to the reaction mixture is added water, and the mixture is extracted with chloroform three times. The extract is washed with an aqueous saturated saline solution, dried over sodium sulfate, and distilled under reduced pressure. The residue is purified by silica gel column chromatography (eluent, chloroform) and recrystallized from ethyl acetate to give (4S)-7,8-dihydro-4-ethyl-6,6-(2,2-dimethyltrimethylenedioxy)-4-hydroxy-1H-pyrano[3,4-f]indolidine-3,10-dione (276 mg) as colorless needles.

Yield: 64% over all in the above (1) and (2)

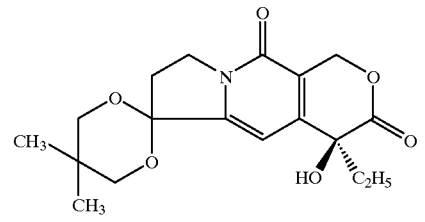

m.p.: 208–210° C.
[α]$_D^{27}$:+88.2° (c=0.99, chloroform)
IR (Nujol, cm$^{-1}$): 3340, 2924, 1744
MS (m/z): 350 (MH$^+$)
NMR (300 MHz, CDCl$_3$, δ): 0.88 (3H, s), 0.99 (3H, t, J=7.3 Hz), 1.29 (3H, s), 1.70–1.92 (2H, m), 2.54 (2H, t, J=7.0 Hz), 3.65-3.69 (4H, m), 3.71 (1H, s), 4.14 (2H, dt, J=3.7 and 7.0 Hz), 5.17 (1H, d, J=16.2 Hz), 5.60 (1H, d, J=16.2 Hz), 6.81 (1H, s)

(3) The (4S)-7,8-diydro-4-ethyl-6,6-(2,2-dimethyltrimethylenedioxy)-4-hydroxy-1H-pyrano[3,4-f]

indolidine-3,10-dione is treated in the same manner as described in Example 1-(5) to give (4S)-7,8-dihydro4-ethyl-4-hydroxy-1H-pyrano[3,4-f]indolidine-3,6,10(4H)-trione.

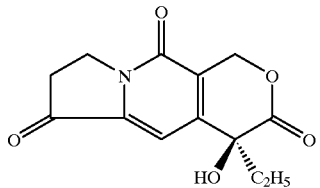

(4) The (4S)-7,8-dihydro-4-ethyl-4-hydroxy-1H-pyrano[3,4-f]-indolidine-3,6,10(4H)-trione is treated in the same manner as described in Example 1-(6) and (8) to give (20S)-7-ethyl-10-[3-(aminopropyloxy)camptothecin hydrochloride.

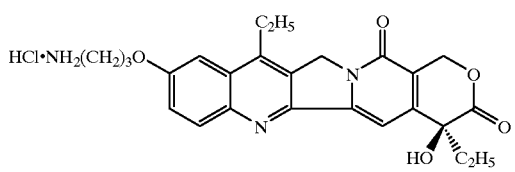

Example 6

(1) Lithium (2S)-2-hydroxy-2-[6-hydroxymethyl-1,1-(2,2-dimethyltrimethylenedioxy)-5-oxo-1,2,3,5-tetrahydro-7-indolidinyl]butyrate obtained in Example 5-(1) is treated in the same manner as described in Example 1-(5) to give (4S)-7,8-dihydro-4-ethyl-4-hydroxy-1H-pyrano[3,4-f]indolidine-3,6,10(4H)-trione.

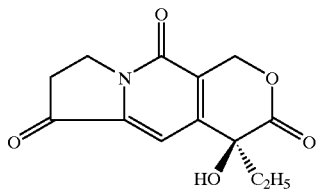

(2) The (4S)-7,8-dihydro-4-ethyl-4-hydroxy-1H-pyrano[3,4-f]indolidine-3,6,10(4H)-trione is treated in the same manner as described in Example 1-(6) and (8) to give (20S)-7-ethyl-10-[3-(aminopropyloxy)camptothecin hydrochloride.

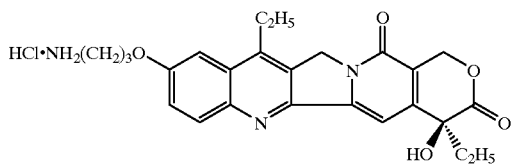

Example 7

(1) The (4S)-7,8-dihydro-4-ethyl-6,6-(2,2-dimethyltrimethylenedioxy)-4-hydroxy-1H-pyrano[3,4-f]indolidine-3,10-dione obtained in Example 5-(2) (50 mg) is dissolved in acetic anhydride (1 ml), and thereto are added pyridine (1 ml) and 4-N,N-dimethylarninopyridine (4 mg) under ice cooling, and the mixture is stirred at room temperature for 23 hours. The reaction mixture is diluted with chloroform, and the mixture is washed with an aqueous citric acid solution, water and an aqueous saturated saline solution, and dried over sodium sulfate. After distilling off the solvent under reduced pressure, the residue is purified by silica gel column chromatography (eluent, chloroform:methanol=40:1) to give (4S)-7,8-dihydro-4-ethyl-6,6-(2,2-dimethyltrimethylenedioxy)-4-acetoxy-1H-pyrano[3,4-f]indolidine-3,10-dione (56 mg) as colorless crystals.

Yield:99%

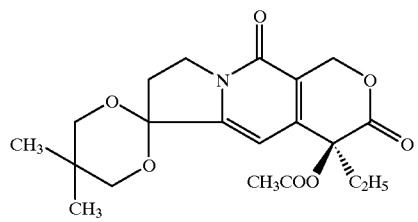

m.p.:185–188° C.
IR (Nujol, cm$^{-1}$): 2922, 2852, 1743, 1671, 1613
MS (m/z): 392 (MH$^+$)
NMR (300 MHz, CDCl$_3$, δ): 0.87 (3H, s), 0.91 (3H, t, J=7.5 Hz), 1.28 (3H, s), 1.95–2.10 (1H, m), 2.15 (3H, s), 2.15–2.28 (1H, m), 2.40–2.61 (2H, m), 3.55–3.73 (4H, m), 4.12 (2H, t, J=6.8 Hz), 5.27 (1H, d, J=17.1 Hz), 5.52 (1H, d, J=17 Hz), 6.31 (1H, s)

(2) The (4S)-7,8-dihydro-4-ethyl-6,6-(2,2-dimethyltrimethylenedioxy)-4-acetoxy-1H-pyrano[3,4-f]indolidine-3,10-dione is treated in the same manner as described in Example 1-(5) to give (4S)-7,8-dihydro-4-ethyl-4-acetoxy-1H-pyrano[3,4-f]indolidine-3,6,10(4H)-trione as colorless crystals.

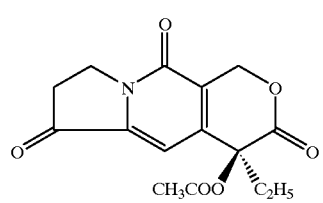

m.p.: 197–203° C.
IR (Nujol, cm$^{-1}$): 1742, 1732,1661, 1610
ESI-MS (0.02M ammonium acetate/methanol, m/z): 323 (MNH$_4^+$)
NMR (300 MHz, CDCl$_3$, δ): 0.92 (3H, t, J=7.5 Hz), 1.94–2.25 (2H, m), 2.16 (3H, s), 2.95 (2H, t, J=6.9 Hz), 4.32 (2H, td, J=6.9 and 0.8 Hz), 5.33 (1H, dd, J=18.1 and 0.5 Hz), 5.60 (1H, dd, J=18.1 and 0.4 Hz), 6.76 (1H, s)

(3) The (4S)-7,8-dihydro-4-ethyl-4-acetoxy-1H-pyrano[3,4-f]indolidine-3,6,10(4H)-trione is treated in the same manner as described in Example 1-(6) to give (20S)-20-O-acetyl-7-ethyl-10-[3-(tert-butoxycarbonylamino)propyloxy]camptothecin as colorless powders.

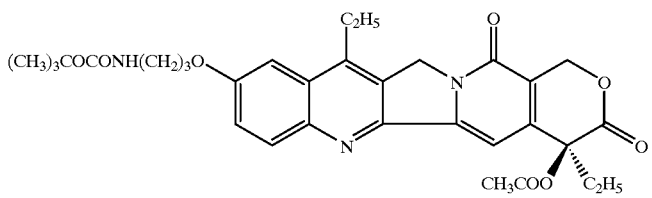

m.p.: 173–176° C.
IR (Nujol, cm$^{-1}$): 3370, 1765, 1749, 1696, 1657
ESI-MS (m/z):592 (MH$^+$)
NMR (300 MHz, CDCl$_3$, δ): 0.97 (3H, t, J=7.5 Hz), 1.39 (3H, t, J=7.7 Hz), 1.45 (9H, s), 2.05–2.32 (4H, m), 2.21 (3H, s), 3.14 (2H, q, J=7.7 Hz), 3.41 (2H, q like, J=6.3 Hz), 4.21 (2H, t, J=6.1 Hz), 4.77 (1H, br), 5.23 (2H, d, J=1.1 Hz), 5.40 (1H, d, J=17.2 Hz), 5.68 (1H, d, J=17.2 Hz), 7.15 (1H, s), 7.33 (1H, d, J=2.6 Hz), 7.47 (1H, dd, J=9.2 and 2.7 Hz), 8.12 (1H, d, J=9.3 Hz)

(4) The (20S)-20-O-acetyl-7-ethyl-10-[3-(tert-butoxycarbonylamino)propyloxy]camptothecin is treated in the same manner as described in Example 1-(7) and (8) to give (20S)-7-ethyl-10-(3-aminopropyloxy)camptothecin hydrochloride.

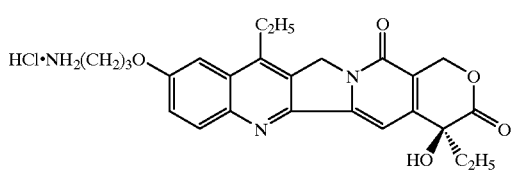

Examples 8–12

(1) The corresponding starting compounds are treated in the same manner as described in Example 1-(1) and (2), there are prepared the compounds as shown in the following Table 1.

TABLE 1

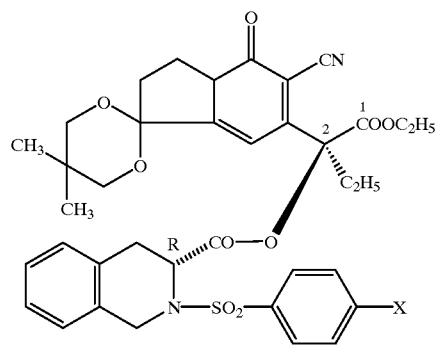

| Ex. No. | X | Diastereoselectivety 2S:2R |
|---|---|---|
| 8 (1) | —Cl | 9.5:1.0 |
| 9 (1) | —CH$_3$ | 9.0:1.0 |

TABLE 1-continued

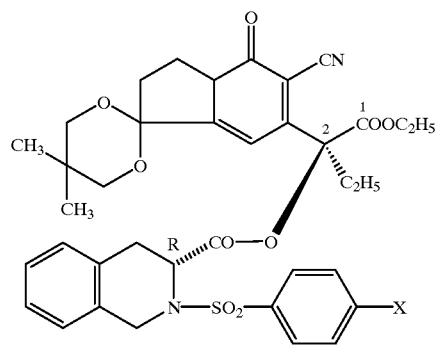

| Ex. No. | X | Diastereoselectivety 2S:2R |
|---|---|---|
| 10 (1) | —OCH$_3$ | 9.0:1.0 |
| 11 (1) | 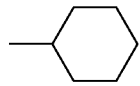 | 9.5:1.0 |
| 12 (1) | 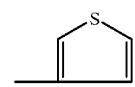 | 10.1:1.0 |

(2) The compounds obtained in the above (1) are treated in the same manner as described in Example 1-(3)–(8) or Example 1-(3)–(5), (7), (6) and (8) to give (20S)-7-ethyl-10-(3-aminopropyloxy)camptothecin hydrochloride.

Examples 13–16

(1) The corresponding starting compounds are treated in the same manner as described in Example 1-(1) and (2), there are prepared the compounds as shown in the following Table 2.

TABLE 2

[Structure: bicyclic compound with dioxane ring bearing two CH3 groups, fused cyclopentane-cyclohexenone with CN and a carbon bearing COOC2H5, OR0, C2H5 groups]

| Ex. No. | R⁰ |
|---|---|
| 13 (1) | [1,2,3,4-tetrahydroisoquinoline with N—Ts, 3-position bearing CO— with R stereochemistry] |
| 14 (1) | [1,2,3,4-tetrahydroisoquinoline with N—SO2-(2,4,6-trimethylphenyl), 3-position bearing CO— with R stereochemistry] |
| 15 (1) | [1,2,3,4-tetrahydroisoquinoline with N—SO2-(2-naphthyl), 3-position bearing CO— with R stereochemistry] |

TABLE 2-continued

[Same core structure as above]

| Ex. No. | R⁰ |
|---|---|
| 16 (1) | [indoline with N—Ts, 2-position bearing CO— with R stereochemistry] |

Ts: Tosyl group (2) The compounds obtained in the above (1) are treated in the same manner as described in Example 1-(3)–(8) or Example 1-(3)–(5), (7), (6) and (8) to give (20S)-7-ethyl-10-(3-aminopropyloxy)camptothecin hydrochloride.

Examples 17–23

The corresponding starting compounds are treated in the same as described in Examples 1, 2, 5 or 7, there are prepared the compounds in the following Table 3.

TABLE 3

[Camptothecin nucleus structure with substituents R⁵¹, R⁶¹, R⁷¹, R⁸¹, R⁹¹ and S-configured carbon bearing HO, CH2CH3]

| Ex. No. | R⁵¹ | R⁶¹ | R⁷¹ | R⁸¹ | R⁹¹ |
|---|---|---|---|---|---|
| 17 | —CH₂—N(piperazine)NH | —H | —O(CH₂)₂O— | | —H |
| 18 | —CH₂NH₂ | —H | —O(CH₂)₂O— | | —H |
| 19 | —CH₂NH₂ | —H | —OCH₂O— | | —H |
| 20 | —H | —NH₂ | —H | —H | —H |
| 21 | 7* —CH(NH₂)CH₂CH₂— | 9* | —CH₃ | —F | —H |
| 22 | —(CH₂)₃— | | —O(CH₂)₃NH₂ | —H | —H |
| 23 | —H | —H | —O(CH₂)₃NH₂ | —H | —H |

*: The number means the substitution position (7-position/9-position) at the camptothecin nucleus.

Example 24

(1) A mixture of ethyl 2-chloro-2-[6-cyano-1,1-(2,2-dimethyltrimethylenedioxy)-5-oxo-1,2,3,5-tetrahydro-7-indolidinyl]acetate (34.11 g), (3R)-N-(4-biphenylylsulfonyl)-1,2,3,4-tetrahydro-3-isoquinolinecarboxylic acid (42.33 g) and potassium carbonate (8.67 g) in dimethylformamide (350 ml) is stirred at 60° C. for 45 minutes. The reaction mixture is ice-cooled, diluted with ethyl acetate (200 ml), and thereto is added an aqueous saturated sodium hydrogen carbonate solution (300 ml) and is further adder water (500 ml). The mixture is extracted with ethyl acetate, and the extract is washed, dried, treated with active carbon and filtered. The solvent is distilled off to give ethyl 2-[[(3R)-N-(4-biphenylyl)-1,2,3,4-tetrahydro-3-isoquinolyl]carbonyloxy]-2-[6-cyano-1,1-(2,2-dimethyltrimethylenedioxy)-5-oxo-1,2,3,5-tetrahydro-7-indolidinyl]acetate (66.20 g) as pale yellow foam.

IR (Nujol, cm$^{-1}$): 2220, 1750, 1665, 1615
MS (m/z): 738 (MH+)
NMR (300 MHz, CDCl$_3$, δ): 0.89 and 0.90 (3H, s), 1.10 and 1.15 (3H, t, J=7 Hz), 1.33 and 1.35 (3H, s), 2.45–2.60 (2H, m), 3.25–3.40 (2H, m), 3.61–3.76 (4H, m), 3.95–4.22 (4H, m), 4.58 and 4.68 (1H, d, J=16 Hz), 4.72 and 4.75 (1H, d, J=16 Hz), 5.22 and 5.29 (1H, dd and t, J=3.6 and 5 Hz), 6.01 and 6.04 (1H, s), 6.58 and 6.65 (1H, s), 7.02–7.20 (4H, m), 7.37–7.51 (3H, m), 7.54–7.60 (2H, m), 7.62–7.68 (2H, m), 7.85–7.93 (2H, m)

(2) The ethyl 2-[[(3R)-N-(4-biphenylylsulfonyl)-1,2,3,4-tetrahydro-3-isoquinolyl]carbonyloxy]-2-[6-cyano-1,1-(2,2-dimethyltrimethylenedioxy)-5-oxo-1,2,3,5-tetrahydro-7-indolidinyl]acetate obtained in the above (1) is treated in the same manner as described in Example 1-(2)–(8) to give (20S)-7-ethyl-10-(3-aminopropyloxy)camptothecin hydrochloride.

Reference Example 1

(1) 6-Cyano-7-methyl-1,5-dioxo-1,2,3,5-tetrahydroindolidine (1.0 g), 2,2-dimethyl-1,3-propanediol (6.64 g) and p-toluenesulfonic acid (15 ml) are mixed in dichloroethane (25 ml), and the mixture is heated under reflux for 17 hours with a reflux apparatus provided with Dean-Stark dehydrating device. The reaction mixture is washed with an aqueous saturated sodium hydrogen carbonate solution and an aqueous saturated saline solution, and dried over magnesium sulfate. After distilling off the solvent under reduced pressure, the residue is purified with a silica gel column chromatography (eluent; chloroform: methanol=50:1) and recrystallized from methanol to give 6-cyano-7-methyl-1,1-(2,2-dimethyltrimethylenedioxy)-5-oxo-1,2,3,5-tetrahydroindolidine (1.05 g) as colorless needles.

Yield: 72%
m.p.: 225–226° C.
IR (Nujol, cm$^{-1}$): 2222, 1645, 1610
MS (m/z): 275 (MH$^+$)
NMR (300 MHz, CDCl$_3$, δ): 0.87 (3H, s), 1.30 (3H, s)2.49 (3H, s), 2.53 (2H, t, J=7 Hz), 3.62 (2H, d, J=11 Hz), 3.69 (2H, d, J=11 Hz), 4.15 (2H, t, J=7 Hz), 6.42 (1H, s)

(2) The 6-cyano-7-methyl-1,1-(2,2-dimethyltrimethylenedioxy)-5-oxo-1,2,3,5-tetrahydroindolidine (14.43 g) is mixed in dry toluene (300 ml) and thereto is added a 60% oily dispersion of sodium hydride (9.26 g, 4.4 equivalents), and the mixture is stirred on a bath of 80° C. for 2 hours. To the reaction mixture are added diethyl carbonate (24.85 g, 4 equivalents) and ethanol (0.97 g, 0.4 equivalent), and the mixture is reacted at 80° C. for 3 hours. While cooling the reaction mixture on an ice bath, a 50% acetic acid (80 ml) is added thereto. The mixture is extracted with chloroform, and the extract is washed with an aqueous saturated saline solution, and dried over magnesium sulfate. After distilling off the solvent under reduced pressure, the residue is purified with a silica gel column chromatography (eluent; chloroform:ethyl acetate 4:1) and recrystallized from ethyl acetate-ether to give ethyl 2-[6-cyano-1,1-(2,2-dimethyltrimethylenedioxy)-5-oxo-1,2,3,5-tetrahydro-7-indolidinyl]acetate (14.63 g) as colorless needles.

Yield:80%
m.p.:150–151° C.
IR (Nujol, cm$^{-1}$): 2220, 1725, 1650, 1610
MS (m/z): 347 (MH$^+$)
NMR (300 MHz, CDCl$_3$, δ): 0.87 (3H, s), 1.28 (3H, s), 1.29 (3H, t, J=7.5 Hz), 2.54 (2H, t, J=7 Hz), 3.62 (2H, d, J=11 Hz), 3.68 (2H, d, J=11 Hz), 3.79 (2H, s), 4.16 (2H, t, J=7 Hz), 4.22 (2H, q, J=7 Hz), 6.54 (1H, s)

(3) The ethyl 2-[6-cyano-1,1-(2,2-dimethyltrimethylenedioxy)-5-oxo-1,2,3,5-tetrahydro-7-indolidinyl]acetate (14.60 g) is added to a suspension of a 60% oily dispersion of sodium hydride (2.02 g, 1.2 equivalent) in dry tetrahydrofuran (240 ml), and the mixture is stirred at room temperature for 3 hours. To the reaction mixture is added bromine (8.76 g, 1.3 equivalent), and the mixture is stirred at room temperature for 2 hours, and thereto is added ice water. The mixture is extracted with chloroform, and the extract is washed with an aqueous sodium thiosulfate solution and an aqueous saturated saline solution, and dried over magnesium sulfate. After distilling off the solvent under reduced pressure, the residue is purified with a silica gel column chromatography (eluent; chloroform:ethyl acetate=4:1) and recrystallized from ethyl acetate-ether to give ethyl 2-bromo-2-[6-cyano-1,1-(2,2-dimethyltrimethylenedioxy)-5-oxo-1,2,3,5-tetrahydro-7-indolidinyl]acetate (15.66 g) as colorless needles.

Yield:87%
m.p.: 117–119° C.
IR (Nujol, cm$^{-1}$): 2217, 1725, 1650, 1610
MS (m/z): 427 (MH$^+$)
NMR (300 MHz, CDCl$_3$, δ): 0.89 (3H, s), 1.28 (3H, s), 1.32 (3H, t, J=7 Hz), 2.54 (2H, t, J=7 Hz), 3.65 (2H, d, J=12 Hz), 3.67 (2H, d, J=12 Hz), 4.09–4.22 (2H, m), 4.24–4.35 (2H, m), 5.61 (1H, s), 6.90 (1H, s)

Reference Example 2

(1) 6-Cyano-7-methyl-1,5-dioxo-1,2,3,5-tetrahydroindolidine (5.93 g), 2,2-diethyl-1,3-propanediol (49.97 g) and p-toluenesulfonic acid (180 ml) are mixed in dichloroethane (150 ml), and the mixture is heated under reflux for 22 hours with a reflux apparatus provided with Dean-Stark dehydrating device. The reaction mixture is treated in the same manner as described in Reference Example 1-(1) and recrystallized from methanol to give 6-cyano-7-methyl-1,1-(2,2-diethyltrimethylenedioxy)-5-oxo-1,2,3,5-tetrahydroindolidine (6.67 g) as colorless needles.

Yield:70%
m.p.: 197–198° C.
IR (Nujol, cm$^{-1}$): 2219, 1655, 1610
MS (m/z): 303 (MH$^+$)
NMR (300 MHz, CDCl$_3$, δ): 0.83 (3H, t, J=7.5 Hz), 0.92 (3H, t, J=7.5 Hz), 1.22 (2H, q, J=7.5 Hz), 1.78 (2H, q, J=7.5 Hz), 2.49 (3H, s), 2.52 (2H, t, J=7 Hz), 3.64 (2H, d, J=11 Hz), 3.78 (2H, d, J=11 Hz), 4.14 (2H, t, J=7 Hz), 6.39 (1H, s)

(2) The procedure of Reference Example 1-(2) is repeated by using 6-cyano-7-methyl-1,1-(2,2-diethyltrimethylenedioxy)-5-oxo-1,2,3,5-tetrahydroindolidine (4.75 g), dry toluene (80 ml), a 60% oily dispersion of sodium hydride (2.76 g, 4.4 equivalents), diethyl carbonate (7.42 g, 4 equivalents) and ethanol (0.37 ml, 0.4 equivalent), and the product is recrystallized from ethyl acetate-ether to give ethyl 2-[6-cyano-1,1-(2,2-diethyltrimethylenedioxy)-5-oxo-1,2,3,5-tetrahydro-7-indolidinyl]acetate (3.71 g) as colorless needles.
Yield:63%
m.p.: 127–129° C.
IR (Nujol, cm$^{-1}$): 2220, 1745, 1660, 1605
MS (m/z): 375 (MH$^+$)
NMR (300 MHz, CDCl$_3$, δ): 0.83 (3H, t, J=7.5 Hz), 0.91 (3H, t, J=7.5 Hz), 1.23 (2H, q, J=7.5 Hz), 1.29 (3H, t, J=7.5 Hz), 1.75 (2H, q, J=7.5 Hz), 2.53 (2H, t, J=7 Hz), 3.62 (2H, d, J=12 Hz), 3.77 (2H, d, J=12 Hz), 3.79 (2H, s), 4.15 (2H, t, J=7 Hz), 4.22 (2H, q, J=7 Hz), 6.50 (1H, s)

(3) The ethyl 2-[6-cyano-1,1-(2,2-diethyltrimethylenedioxy)-5-oxo-1,2,3,5-tetrahydro-7-indolidinyl]acetate (3.52 g) is added to a suspension of a 60% oily dispersion of sodium hydride (451 mg, 1.2 equivalent) in dry tetrahydrofuran (60 ml), and the mixture is treated at room temperature for 3 hours. To the reaction mixture is added bromine (1.95 g, 1.3 equivalent), and the mixture is stirred at room temperature for 3 hours, and the reaction mixture is treated in the same manner as described in Reference Example 1-(3) and recrystallized from ethyl acetate-ether to give ethyl 2-bromo-2-[6-cyano-1,1-(2,2-diethyltrimethylenedioxy)-5-oxo-1,2,3,5-tetrahydro-7-indolidinyl]acetate (2.45 g) as colorless needles.
Yield:58%
m.p.: 106–108° C.
IR (Nujol, cm$^{-1}$): 2220, 1735,1660, 1610
MS (m/z): 455 (MH$^+$)
NMR (300 MHz, CDCl$_3$, δ): 0.83 (3H, t, J=7.5 Hz), 0.92 (3H, t, J=7.5 Hz), 1.26 (2H, q, J=7.5 Hz), 1.32 (3H, t, J=7 Hz), 1.73 (2H, q, J=7.5 Hz), 2.52 (2H, t, J=7 Hz), 3.61 (1H, d, J=12 Hz), 3.62 (1H, d, J=12 Hz), 3.77 (1H, dd, J=2 and 12 Hz), 3.80 (1H, dd, J=2 and 12 Hz), 4.16 (2H, m), 4.25–4.35 (2H, m), 5.61 (1H, s), 6.85 (1H, s)

Reference Example 3

Sodium hydroxide (13.6 g) is dissolved in water (300 ml), and therein is suspended (3R)-1,2,3,4-tetrahydro-3-isoquinolinecarboxylic acid (30.0 g) and thereto is added tetrahydrofuran (120 ml). To the resulting solution is added 4-biphenylylsulfonyl chloride (42.9 g), and the mixture is stirred at room temperature for one hour. The reaction mixture is acidified with 10% hydrochloric acid under ice cooling, and is diluted with water, and then extracted twice with ethyl acetate. The extract is washed with water and an aqueous saturated saline solution, dried over sodium sulfate and then treated with active carbon. Undissolved materials are filtered off from the extract, and the solvent is distilled off under reduced pressure. The residue is recrystallized from ethyl acetate-hexane to give (3R)-N-(4-biphenylylsulfonyl)-1,2,3,4-tetrahydro-3-isoquinolinecarboxylic acid (36.5 g) as colorless crystals.
Yield:55%
m.p.: 195–202° C.
$[α]_D^{29}$:+8.02° (c=1.08, dimethylformamide)
IR (Nujol, cm$^{-1}$): 3300, 2924, 1743, 1456
MS (m/z): 394 (MH$^+$)
NMR (300 MHz, CDCl$_3$, δ): 3.10–3.15 (2H, m), 4.48 (1H, d, J=15.6 Hz), 4.67 (1H, d, J=15.6 Hz), 4.93 (1H, dd, J=4.0 and 5.3 Hz), 6.95–7.20 (4H, m), 7.40–7.53 (3H, m), 7.56–7.69 (4H, m), 7.83–7.88 (2H, m)

Reference Example 4

(3R)-1,2,3,4-Tetrahydro-3-isoquinolinecarboxylic acid (5.32 g) and sodium hydroxide (2.40 g) are added to a mixture of methylene chloride-water (200 ml—200 ml), and thereto is added dropwise a solution of 4-nitrophenylsulfonyl chloride (6.62 g) in methylene chloride (100 ml) under ice cooling over a period of 30 minutes. The mixture is stirred under ice cooling for 3 hours, and thereto are further added sodium hydroxide (1.20 g) and a solution of 4-nitrophenylsulfonyl chloride (3.32 g) in methylene chloride (60 ml) in this order. The mixture is stirred under ice cooling for 2 hours, and further stirred at room temperature for 17 hours, and the reaction mixture is diluted with chloroform and 10% hydrochloric acid. The chloroform layer is collected and washed with water and then with an aqueous saturated saline solution, dried over sodium sulfate and then treated with active carbon. Undissolved materials are filtered off from the chloroform layer, and the solvent is distilled off under reduced pressure. The residue is purified with a silica gel column chromatography (eluent, chloroform) and recrystallized from ethyl acetate-hexane to give (3R)-N-(4-nitrophenylsulfonyl)-1,2,3,4-tetrahydro-3-isoquinolinecarboxylic acid (4.01 g) as colorless crystals.
Yield:37%
m.p.:140° C.
$[α]_D^{25}$:+27.2° (c=0.5, ethanol)
IR (Nujol, cm$^{-1}$): 3316, 1743, 1531, 1169
MS (m/z): 361 (M-H$^+$)
NMR (300 MHz, CDCl$_3$, δ): 3.15–3.30 (2H, m), 4.40 (1H, d, J=15 Hz), 4.73 (1H, d, J=15 Hz), 5.01 (1H, dd, J=3.7 and 5.7 Hz), 7.04–7.20 (4H, m), 7.99 (2H, d, J=9.0 Hz), 8.20 (2H, d, J=9.0 Hz)

Reference Example 5

To a suspension of ethyl 2-[6-cyano-1,1-(2,2-dimethyltrimethylenedioxy-5-oxo-1,2,3,5-tetrahydro-7-indolidinyl]acetate (43.41 g) in tetrahydrofuran (600 ml) is added triethylamine (13.94 g) under argon atmosphere at −4° C. and thereto is further added dropwise trimethylsilyl chloride (14.41 g) at −4 to −3° C. over a period of 5 minutes. The mixture is stirred at the same temperature for 55 minutes and thereto is added dropwise a suspension of N-chlorosuccinimide (17.00 g) in tetrahydrofuran (400 ml) at −4 to 4° C. over a period of 7 minutes. The reaction mixture is further stirred at a temperature of 0° C. to 4° C. for 4.5 hours, and thereto added water (1 liter) at 0° C., and the mixture is extracted with ethyl acetate. The extract is washed, dried, treated with active carbon, filtered and then distilled to remove the solvent. The residue is recrystallized from ethyl acetate-isopropyl ether to give ethyl 2-chloro-2-[6-cyano-1,1-(2,2-dimethyltrimethylenedioxy)-5-oxo-1,2,3,5-tetrahydro-7-indolidinyl]acetate (40.28 g) as colorless needles.
Yield:84%
m.p.: 153–155° C.
IR (Nujol, cm$^{-1}$): 2227, 1749, 1662, 1615,1541, 1311, 1241, 1202, 1179, 1161, 1143, 1065, 967, 835, 715
APCIMS (m/z): 381 and 383 (MH$^+$)
NMR (300 MHz, CDCl$_3$, δ): 0.88 (3H, s), 1.28 (3H, s), 1.31 (3H, t, J=7.1 Hz), 2.52–2.58 (2H, m), 3.60–3.70 (4H, m), 4.13–4.21 (2H, m), 4.22–4.37 (2H, m), 5.63 (1H,s), 6.77 (1H, s)

Reference Example 6

(1) 3-Aminopropanol (6.0 g) is dissolved in methylene chloride (50 ml) and thereto is added dropwise di-t-butyl dicarbonate (18.3 g) with stirring under ice cooling. The mixture is stirred at room temperature for 2 hours, and the reaction mixture is concentrated and then purified with a silica gel column chromatography to give 3-t-butoxycarbonylaminopropanol (13.98 g) as colorless oil.

Yield:99.9%
IR (Neat), $v_{max}$ cm$^{-1}$:3380, 1790
MS (m/z): 176 (M+H$^+$)
NMR (300 MHz, CDCl$_3$, δ):1.45 (9H, s), 1.62–1.72 (2H, m), 3.0 (1H, brs.), 3.29 (2H, dd, J=12 Hz and 6 Hz), 3.66 (2H, dd, J=12 Hz and 6 Hz), 4.80 (1H, brs)

(2) 3-t-Butoxycarbonylaminopropanol (10.0 g) is dissolved in methylene chloride (100 ml) and thereto are added triethylamine (8.66 g) and tosyl chloride (16.3 g) with stirring under ice cooling. The mixture is stirred at room temperature overnight. The reaction mixture is concentrated and the residue is dissolved in water-ethyl acetate, and the organic layer is separated, washed with an aqueous saturated saline solution, dried over sodium sulfate, and then distilled off the solvent. The residue is purified with a silica gel column chromatography to give 3-t-butoxycarbonylaminopropyl tosylate (15.37 g) as pale yellow oil.
Yield:82%
IR (Neat), $v_{max}$ cm$^{-1}$:3400, 3340, 1700, 1600
MS (m/z): 352 (M+Na$^+$)
NMR (300 MHz, CDCl$_3$, δ): 1.42 (9H, s), 1.78–1.90 (2H, m), 2.45 (3H, s), 3.11–3.22 (2H, m), 4.09 (2H, t, J=6 Hz), 4.5–4.65 (1H, m), 7.36 (2H, d, J=8 Hz), 7.77–7.83 (2H, m)

(3) 5-Hydroxy-2-nitrobenzaldehyde (60 g) is dissolved in dry tetrahyrofuran (90 ml) and thereto is added dropwise vinylmagnesium bromide (2.3 equivalents) with stirring at −78° C. The temperature of the reaction mixture is raised gradually. After completion of the reaction, 1N HCl is added to the reaction mixture, and the mixture is extracted with ethyl acetate, and the organic layer is separated, washed with an aqueous saturated saline solution, dried over sodium sulfate, and then distilled off the solvent. The residue is purified with a silica gel column chromatography to give 1-(5'-hydroxy-2'-nitrophenyl)-2-propen-1-ol (5.09 g) as yellowish brown powders.
Yield:73%
m.p.: 126–130° C.
IR (Nujol), $v_{max}$ cm$^{-1}$: 3440, 1600
MS (m/z): 195 (M$^+$)
NMR (300 MHz, CDCl$_3$, δ): 2.4 (1H, br), 5.19 (1H, dd, J=10.5 Hz and 1.5 Hz), 5.38 (1H, dd, J=17 Hz and 1.5 Hz), 5.89 (1H, m), 6.08 (1H, ddd, J=17 Hz, 10.5 Hz and 5 Hz), 6.80 (1H, dd, J=9 Hz and 3 Hz), 7.22 (1H, d, J=3 Hz), 7.97 (1H, d, J=9 Hz), 9.90 (1H, brs)

(4) 1-(5'-Hydroxy-2'-nitrophenyl)-2-propen-1-ol (2.0 g) is dissolved in dry dimethylformamide (100 ml) and thereto are added sodium iodide (1 equivalent) and potassium carbonate and 3-t-butoxycarbonylaminopropyl tosylate (1.5 equivalent). The mixture is stirred at 50° C. for 6 hours, and thereto is added ethyl acetate. The mixture is washed with an aqueous saturated saline solution, dried over sodium sulfate. After distilling off the solvent, the residue is purified with a silica gel column chromatography to give 1-[5'-(3"-t-butoxycarbonylaminopropyloxy)-2'-nitrophenyl]-2-propen-1-ol (3.53 g) as pale brown caramel.
Yield:98%
IR (Neat), $v_{max}$ cm$^{-1}$: 3400, 1690, 1680
MS (m/z): 375 (M+Na$^+$)
NMR (300 MHz, CDCl$_3$, δ): 1.44 (9H, s), 1.96–2.06 (2H, m), 2.80 (1H, brs), 3.33 (2H, q, J=6.5 Hz), 4.11 (2H, t, J=6 Hz), 4.8 (1H, brs), 5.24 (1H, dd, J=10.5 Hz and 1.5 Hz), 5.42 (1H, dd, J=17 Hz and 1.5 Hz), 5.92 (1H, d, J=5 Hz), 6.08 (1H, ddd, J=17 Hz, 10.5 Hz and 5 Hz), 6.86 (1H, dd, J=9 Hz and 3 Hz), 7.25 (1H, d, J=3 Hz), 8.04 (1H, d, J=9 Hz)

(5) 1-(5'-(3"-t-butoxycarbonylaminopropyloxy)-2'-nitrophenyl)-2-propen-1-ol (9.66 g) is dissolved in chloroform (300 ml) and thereto is added activated manganese dioxide (7.2 g), and the mixture is heated with reflux. After completion of the reaction, inorganic materials are filtered off with celite, and the filtrate is concentrated, and thereto is added ethyl acetate. The organic layer is separated, washed with an aqueous saturated saline solution, dried over sodium sulfate. After distilling off the solvent, the residue is purified with a silica gel column chromatography to give 1-[5'-(3"-t-butoxycarbonylaminopropyloxy)-2'-nitrophenyl]-2-propen-1-one (6.01 g) as yellow color crystal.
m.p.: 65–71° C.
Yield:63%
IR (Neat), $v_{max}$ cm$^{-1}$:3350, 1700
MS (m/z):351 (M+H$^+$)
NMR (300 MHz, CDCl$_3$,δ): 1.44 (9H, s), 1.98–2.18 (2H, m), 3.28–3.37 (2H, q, J=6.5 Hz), 4.08–4.16 (2H, m), 4.67 (1H, brs), 5.85 (1H, d, J=17.5 Hz), 6.02 (1H, d, J=10.5 Hz), 6.62 (1H, dd, J=17.5 Hz and 10.5 Hz), 6.82 (1H, d, J=3 Hz), 7.03 (1H, dd, J=9 Hz and 3 Hz), 8.17 (1H, d, J=9 Hz)

(6) 1-[5'-(3"-t-butoxycarbonylaminopropyloxy)-2'-nitrophenyl)-2-propen-1-one (325 mg) is dissolved in ethanol (15 ml) and thereto is added 10% palladium-carbon (40 mg), and the mixture is stirred under hydrogen atmosphere for 1.5 hour. After removing the catalyst by filtration, the filtrate is concentrated and purified with a silica gel column chromatography to give 1-[5'-(3"-t-butoxycarbonylaminopropyloxy)-2'-aminophenyl]propan-1-one (248 mg) as yellow powders.
m.p.:112–115° C.
Yield:83%
IR (Nujol), $v_{max}$ cm$^{-1}$: 3450, 3400, 3340, 1700, 1650
MS (m/z): 323 (M+H$^+$)
NMR (300 MHz, CDCl$_3$, δ): 1.21 (3H, t, J=7 Hz), 1.45 (9H, s), 1.90–2.01 (2H, m), 2.95 (2H, q,J=7.5 Hz), 3.33 (2H, q, J=6.5 Hz), 3.97 (2H, t, J=6.5 Hz), 4.48 (1H, brs), 5.96 (2H, brs), 6.62 (1H, d, J=9 Hz), 6.95 (1H, dd, J=9 Hz and 3 Hz), 7.24 (1H, d, J=3 Hz)

What is claimed is:

1. A 2-substituted hydroxy-2-indolidinylacetic ester compound of the formula [I]:

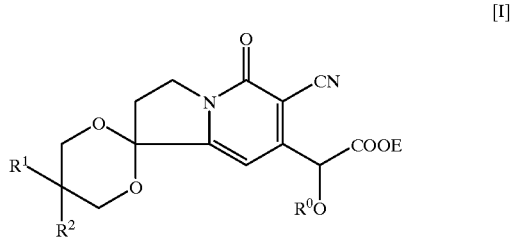

wherein R$^0$ is a residue of a nitrogen-containing fused heterocyclic carboxylic acid having an absolute configuration of "R" which is obtained by removing hydroxy group from the carboxyl group of said carboxylic acid (in which the nitrogen atom contained in the residue is protected), R$^1$ and R$^2$ are a lower alkyl group, and E is an ester residue.

2. An S type 2-substituted hydroxy-2-indolidinylbutyric ester compound of the formula [II]:

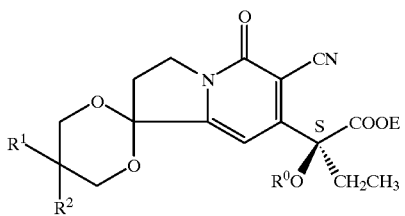

wherein R⁰ is a residue of a nitrogen-containing fused heterocyclic carboxylic acid having an absolute configuration of "R" which is obtained by removing hydroxy group from the carboxyl group of said carboxylic acid (in which the nitrogen atom contained in the residue is protected), $R^1$ and $R^2$ are a lower alkyl group, and E is an ester residue.

3. An S type 2-substituted hydroxy-2-(6-substituted aminomethylindolidinyl)butyric ester compound of the formula [V]:

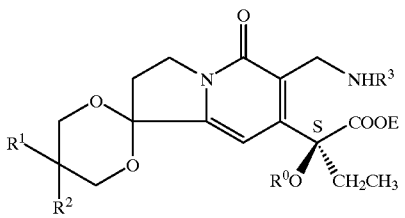

wherein R⁰ is a residue of a nitrogen-containing fused heterocyclic carboxylic acid having an absolute configuration of "R" which is obtained by removing hydroxy group from the carboxyl group of said carboxylic acid (in which the nitrogen atom contained in the residue is protected), $R^1$ and $R^2$ are a lower alkyl group, E is an ester residue, and $R^3$ is a lower alkanoyl group.

4. An S type 2-substituted hydroxy-2-(6-substituted hydroxymethylindolidinyl)butyric ester compound of the formula [VI]:

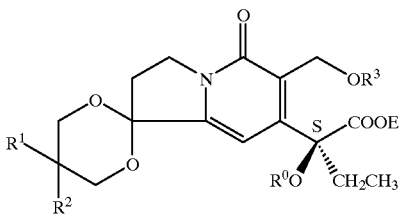

wherein R⁰ is a residue of a nitrogen-containing fused heterocyclic carboxylic acid having an absolute configuration of "R" which is obtained by removing hydroxy group from the carboxyl group of said carboxylic acid (in which the nitrogen atom contained in the residue is protected), $R^1$ and $R^2$ are a lower alkyl group, E is an ester residue, and $R^3$ is a lower alkanoyl group.

5. A compound of the formula:

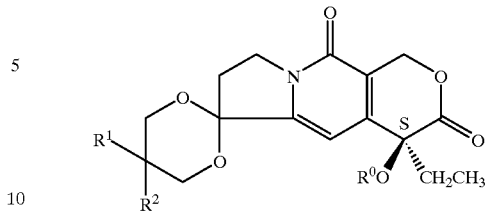

wherein R⁰ is a residue of a nitrogen-containing fused heterocyclic carboxylic acid having an absolute configuration of "R" which is obtained by removing hydroxy group from the carboxyl group of said carboxylic acid (in which the nitrogen atom contained in the residue is protected), and $R^1$ and $R^2$ are a lower alkyl group.

6. An S type 2-hydroxy-2-(6-hydroxymethylindolidinyl)butyric acid compound of the formula [IX]:

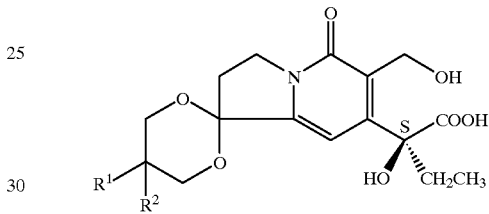

wherein $R^1$ and $R^2$ are a lower alkyl group, or a salt thereof.

7. An S type 4-hydroxypyranoindolidine compound of the formula [X]:

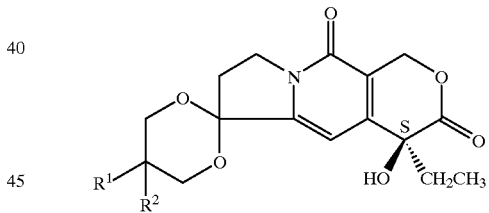

wherein $R^1$ and $R^2$ are a lower alkyl group, or a salt thereof.

8. An S type 4-alkanoyloxypyranoindolidine compound of the formula [XII]:

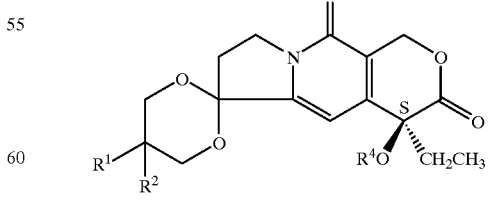

wherein $R^1$ and $R^2$ are a lower alkyl group, and $R^4$ is a lower alkanoyl group.

9. A 2-halogeno-2-indolidinylacetic ester compound of the formula [III]:

[III]
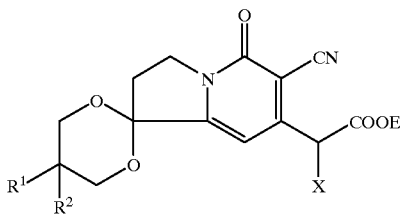
wherein X is a halogen atom, $R^1$ and $R^2$ are a lower alkyl group, and E is an ester residue.
10. An indolidinylmethane compound of the formula [XXVI]:
[XXVI]
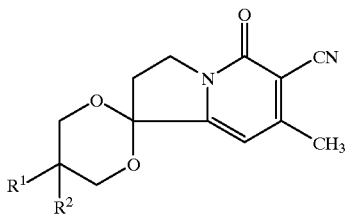
wherein $R^1$ and $R^2$ are a lower alkyl group.
11. A 2-indolidinylacetic ester compound of the formula [XXVIII]:
[XXVIII]
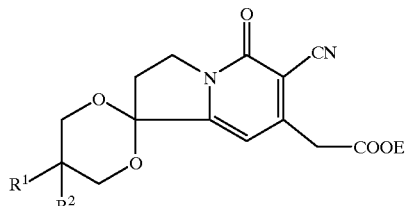
wherein $R^1$ and $R^2$ are a lower alkyl group, and E is an ester residue.
* * * * *

UNITED STATES PATENT AND TRADEMARK OFFICE
CERTIFICATE OF CORRECTION

PATENT NO.    : 6,114,529
DATED         : September 5, 2000
INVENTOR(S)   : Takayuki Kawaguchi et al.

It is certified that error appears in the above-identified patent and that said Letters Patent is hereby corrected as shown below:

Title page,
Item [62], Related U.S. Application Data,
Please insert after "No. 6,015,901" -- , which is a division of application No. 08/958,979, Oct. 28, 1997, Pat. No. 5,932,732 --.

Column 1,
Line 9, please insert after "No. 6,015,901" -- , which is a division of application No. 08/958,979, Oct. 28, 1997, Pat. No. 5,932,732 --.

Signed and Sealed this

Eighteenth Day of December, 2001

*Attest:*

JAMES E. ROGAN
*Attesting Officer*        *Director of the United States Patent and Trademark Office*